US008956662B2

(12) United States Patent
Monteith et al.

(10) Patent No.: US 8,956,662 B2
(45) Date of Patent: Feb. 17, 2015

(54) PHENYLEPHRINE PHARMACEUTICAL FORMULATIONS AND COMPOSITIONS FOR COLONIC ABSORPTION

(75) Inventors: David Monteith, Pittstown, NJ (US); John O'Mullane, Mountain Lakes, NJ (US); Joseph P. Reo, Lakeland, TN (US); Robert T. Nowak, New Providence, NJ (US); Jiansheng Wan, Springfield, NJ (US); Mohammed A. Kabir, Lakeland, TN (US); Malaz A. Abutarif, North Brunswick, NJ (US); Glenn E. Fritz, Arlington, TN (US)

(73) Assignee: MSD Consumer Care, Inc., Memphis, TN (US)

( * ) Notice: Subject to any disclaimer, the term of this patent is extended or adjusted under 35 U.S.C. 154(b) by 1157 days.

(21) Appl. No.: 11/756,881

(22) Filed: Jun. 1, 2007

(65) Prior Publication Data
US 2008/0020055 A1    Jan. 24, 2008

Related U.S. Application Data

(60) Provisional application No. 60/810,021, filed on Jun. 1, 2006, provisional application No. 60/874,830, filed on Dec. 14, 2006.

(51) Int. Cl.
*A61K 31/137* (2006.01)
*A61K 31/4545* (2006.01)
(Continued)

(52) U.S. Cl.
CPC ............... *A61K 9/2054* (2013.01); *A61K 9/209* (2013.01)
USPC ........... 424/497; 424/490; 424/452; 424/468; 514/290; 514/653

(58) Field of Classification Search
USPC ........... 424/497, 490, 452, 468; 514/290, 653
See application file for complete search history.

(56) References Cited

U.S. PATENT DOCUMENTS

| 3,492,397 A | 1/1970 | Peters et al. |
| 3,558,768 A | 1/1971 | Klippel |

(Continued)

FOREIGN PATENT DOCUMENTS

| AU | B-56761-86 | 5/1989 |
| EP | 2 08 855 | 6/1991 |

(Continued)

OTHER PUBLICATIONS

Hamdani, J. et al. "Development and evaluation of prolonged release pellets obtained by the melt pelletization process", *Int'l J. Pharmaceutics* (2002) pp. 167-177, vol. 245.

(Continued)

*Primary Examiner* — Ernst V Arnold
*Assistant Examiner* — Hong Yu
(74) *Attorney, Agent, or Firm* — Catherine D. Fitch; Dianne Pecoraro

(57) ABSTRACT

The invention discloses a pharmaceutical composition comprising phenylephrine or a pharmaceutically acceptable salt thereof and an erodible layer which is for oral administration wherein the composition delivers phenylephrine or a pharmaceutically acceptable salt thereof via absorption in the colon. The pharmaceutical composition comprises a core comprising phenylephrine or a pharmaceutically acceptable salt thereof and an erodible layer which is in a time-dependent, pH-dependent, or colon-specific enzyme-dependent erodible layer that degrades to expose the core to release phenylephrine in the colon. In one preferred embodiment, the erodible layer encases the core. The composition optionally further comprises phenylephrine in the erodible layer or other additional layer(s). The pharmaceutical composition can further comprise one or more additional therapeutically active agents selected from one or more of the group consisting of antihistamines, analgesics, anti-pyretics, and non-steroidal anti-inflammatory agents. The invention also discloses methods of administering phenylephrine via the colon, thereby increasing the bioavailable amount of therapeutically active unconjugated phenylephrine relative to the total phenylephrine in the plasma.

9 Claims, 9 Drawing Sheets

(51) Int. Cl.
*A61K 9/14* (2006.01)
*A61P 11/02* (2006.01)
*A61P 31/16* (2006.01)
*A61P 37/00* (2006.01)
*A61K 9/48* (2006.01)
*A61K 9/22* (2006.01)
*A61K 9/24* (2006.01)
*A61K 9/20* (2006.01)

(56) References Cited

U.S. PATENT DOCUMENTS

| | | | |
|---|---|---|---|
| 3,696,188 A * | 10/1972 | Fernandez et al. | 424/471 |
| 3,851,051 A | 11/1974 | Miskel et al. | |
| 4,282,233 A | 8/1981 | Vilani | |
| 4,294,820 A | 10/1981 | Keith et al. | |
| 4,623,664 A | 11/1986 | Schoenwald et al. | |
| 4,659,716 A | 4/1987 | Vilani et al. | |
| 4,764,378 A | 8/1988 | Keith et al. | |
| 4,792,452 A | 12/1988 | Howard et al. | |
| 4,816,264 A | 3/1989 | Phillips et al. | |
| 5,025,019 A | 6/1991 | Sunshine et al. | |
| 5,085,865 A | 2/1992 | Nayak | |
| 5,133,974 A | 7/1992 | Paradissis et al. | |
| 5,229,134 A * | 7/1993 | Mention et al. | 424/482 |
| 5,458,879 A | 10/1995 | Singh et al. | |
| 5,518,730 A | 5/1996 | Fuisz | |
| 5,681,584 A * | 10/1997 | Savastano et al. | 424/473 |
| 5,876,752 A | 3/1999 | Herbig et al. | |
| 6,071,958 A | 6/2000 | Jimenez-Bayardo et al. | |
| 6,090,411 A | 7/2000 | Pillay et al. | |
| 6,114,346 A | 9/2000 | Harris et al. | |
| 6,160,020 A | 12/2000 | Ohannesian et al. | |
| 6,265,414 B1 | 7/2001 | Harris et al. | |
| 6,267,986 B1 | 7/2001 | Jain et al. | |
| 6,358,525 B1 | 3/2002 | Guo et al. | |
| 6,562,363 B1 | 5/2003 | Mantelle et al. | |
| 6,602,521 B1 | 8/2003 | Ting et al. | |
| 6,709,676 B2 | 3/2004 | Cho | |
| 6,955,821 B2 | 10/2005 | Davis et al. | |
| 6,979,463 B2 | 12/2005 | Kuo | |
| 7,378,082 B1 | 5/2008 | Krishnamoorthy | |
| 2001/0011102 A1 | 8/2001 | Weinstein et al. | |
| 2003/0049319 A1 | 3/2003 | Sriwongjanya et al. | |
| 2003/0083354 A1 | 5/2003 | Kiel et al. | |
| 2003/0086971 A1 | 5/2003 | Kou | |
| 2003/0114535 A1 | 6/2003 | Redkar et al. | |
| 2003/0133978 A1 | 7/2003 | Davis et al. | |
| 2003/0175342 A1* | 9/2003 | Kolter et al. | 424/468 |
| 2003/0180362 A1 | 9/2003 | Park et al. | |
| 2003/0203027 A1* | 10/2003 | Verreck et al. | 424/471 |
| 2003/0236275 A1 | 12/2003 | Salmun et al. | |
| 2004/0122022 A1 | 6/2004 | Gonzales et al. | |
| 2004/0214215 A1 | 10/2004 | Yu et al. | |
| 2005/0026890 A1 | 2/2005 | Robinson et al. | |
| 2005/0069580 A1* | 3/2005 | Hirsh et al. | 424/452 |
| 2005/0090454 A1 | 4/2005 | Robinson et al. | |
| 2005/0095288 A1 | 5/2005 | Honea | |
| 2005/0152967 A1 | 7/2005 | Tengler et al. | |
| 2005/0220877 A1 | 10/2005 | Patel et al. | |
| 2005/0266032 A1 | 12/2005 | Srinivasan et al. | |
| 2005/0281875 A1* | 12/2005 | Srinivasan et al. | 424/472 |
| 2006/0057205 A1 | 3/2006 | Srinivasan et al. | |
| 2006/0073189 A1 | 4/2006 | Pinney et al. | |
| 2006/0127473 A1 | 6/2006 | Nichols | |
| 2006/0159761 A1 | 7/2006 | Kou | |
| 2006/0280795 A1* | 12/2006 | Penhasi et al. | 424/472 |
| 2007/0197661 A1 | 8/2007 | Bubnis et al. | |
| 2008/0014274 A1 | 1/2008 | Bunbis et al. | |
| 2008/0026055 A1 | 1/2008 | Fubara et al. | |

FOREIGN PATENT DOCUMENTS

| | | | |
|---|---|---|---|
| EP | 0 396 404 B1 | 2/1994 | |
| RU | 2 22 0 740 | 10/2004 | |
| WO | WO 95/20946 | 8/1995 | |
| WO | WO 98/18470 * | 5/1998 | A61K 31/445 |
| WO | WO 00/50015 | 8/2000 | |
| WO | WO 03/059327 | 7/2003 | |
| WO | WO 2005/120465 A2 | 12/2005 | |
| WO | WO 2006/064327 | 6/2006 | |
| WO | WO 2007/052299 A2 | 5/2007 | |
| WO | WO 2008/008364 | 1/2008 | |
| WO | WO 2008/064192 | 5/2008 | |

OTHER PUBLICATIONS

International Search Report for PCT/US2007/013048, International Filing Date Jan. 6, 2007, 4 pgs.

International Search Report for PCT/US2007/013056, International Filing Date Jan. 6, 2007, 4 pgs.

International Search Report for PCT/US2007/013050, International Filing Date Jan. 6, 2007, 6 pgs.

Invitation to Pay Additional Fees for PCT/US2007/013047, International Filing Date Jan. 6, 2007, 5pgs.

Rebekah Moan, (3"Health News Daily", Sep. 27, 2006), (1pg.) Waxman: Schering-Plough Phenylephrine Study Results Support FDA "Inquiry".

FDA Webview, "Reformulated Cold Medicines Ineffective: Researcher" (1 pg) Feb. 1, 2007.

Sphere, "Schering-plough Releases Study Data on Phenylephrine" (4pgs.), Nov. 6, 2006, http://sphere.us.schp.com/news/current/main.jsp?id=18179.

Shah, V. P. et al, Pharmaceutical Research, (1998) vol. 15 (6) pp. 889-896.

Moore, et al., "Mathematical Comparison of Dissolution Profiles", Pharmaceutical Technology, Jun. 1996, pp. 64-74.

T'Chueshova, V.I., Kharkov, 2002, vol. 2, pp. 330-334, 356.

Baveja, et al., "Zero-order release hydrophilic matrix tablets of B-adrenergic blockers", Int'l J. Pharmaceutics, vol. 39 (1987) pp. 39-45.

Hamdani et al. "Development and evaluation of prolonged release pellets obtained by the melt pelletization process" Int'l J. Pharm. Oct. 1, 2002; vol. 245 No. 1-2; pp. 167-177.

Hamdani, et al. "Physical and thermal characterisation of Precirol® and Compritol® as lipophilic glycerides used for the preparation of controlled-release matrix pellets." Int J. Pharm. Jul. 9, 2003; vol. 260(1); pp. 47-57.

Marlin, et al. "Major degradation product identified in several pharmaceutical formulations against the common cold." Anal Chem; 2005; vol. 77(2); pp. 471-477.

Hendeles L., "Selecting a decongestant." Pharmacotherapy. 1993; vol. 13(6); pp. 129S-143S.

Garcia, et al. "Poly(ethyleneglycol) column for the determination of acetaminophen, phenylephrine and chlorpheniramine in pharmaceutical formulations." J Chrom. B; Mar. 5, 2003; vol. 785(2); pp. 237-243.

* cited by examiner

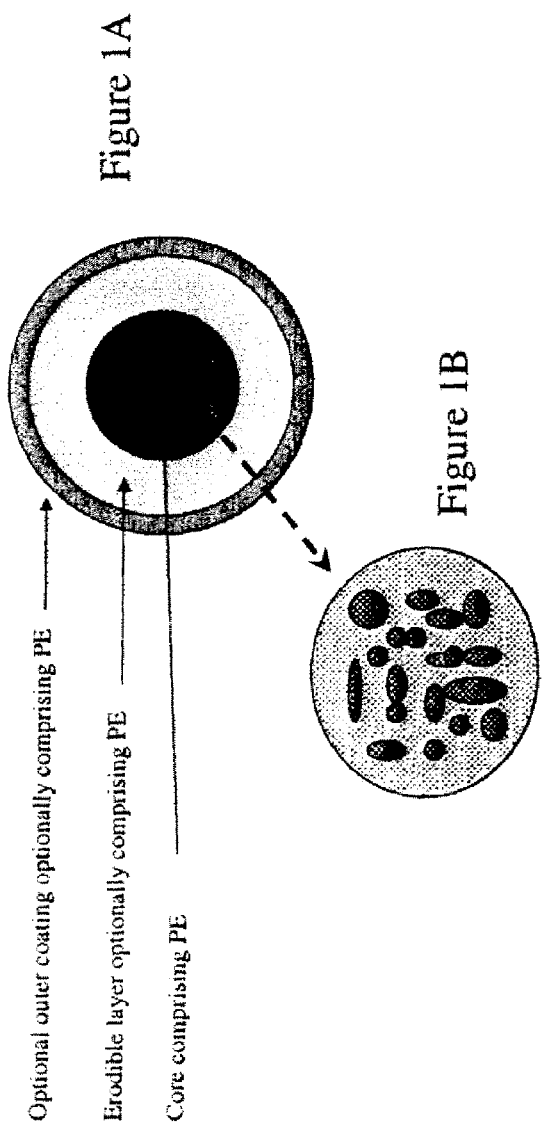
Figure 1A
Figure 1B
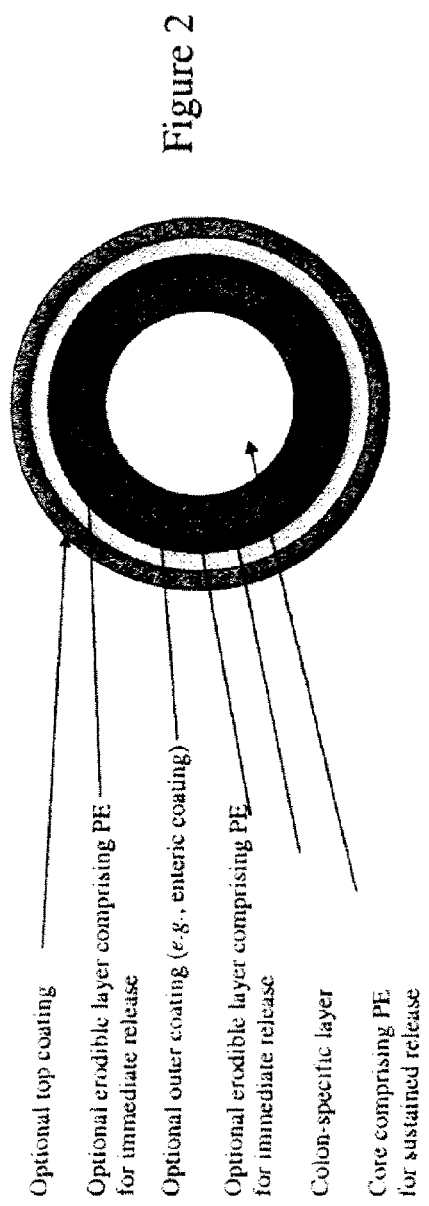
Figure 2

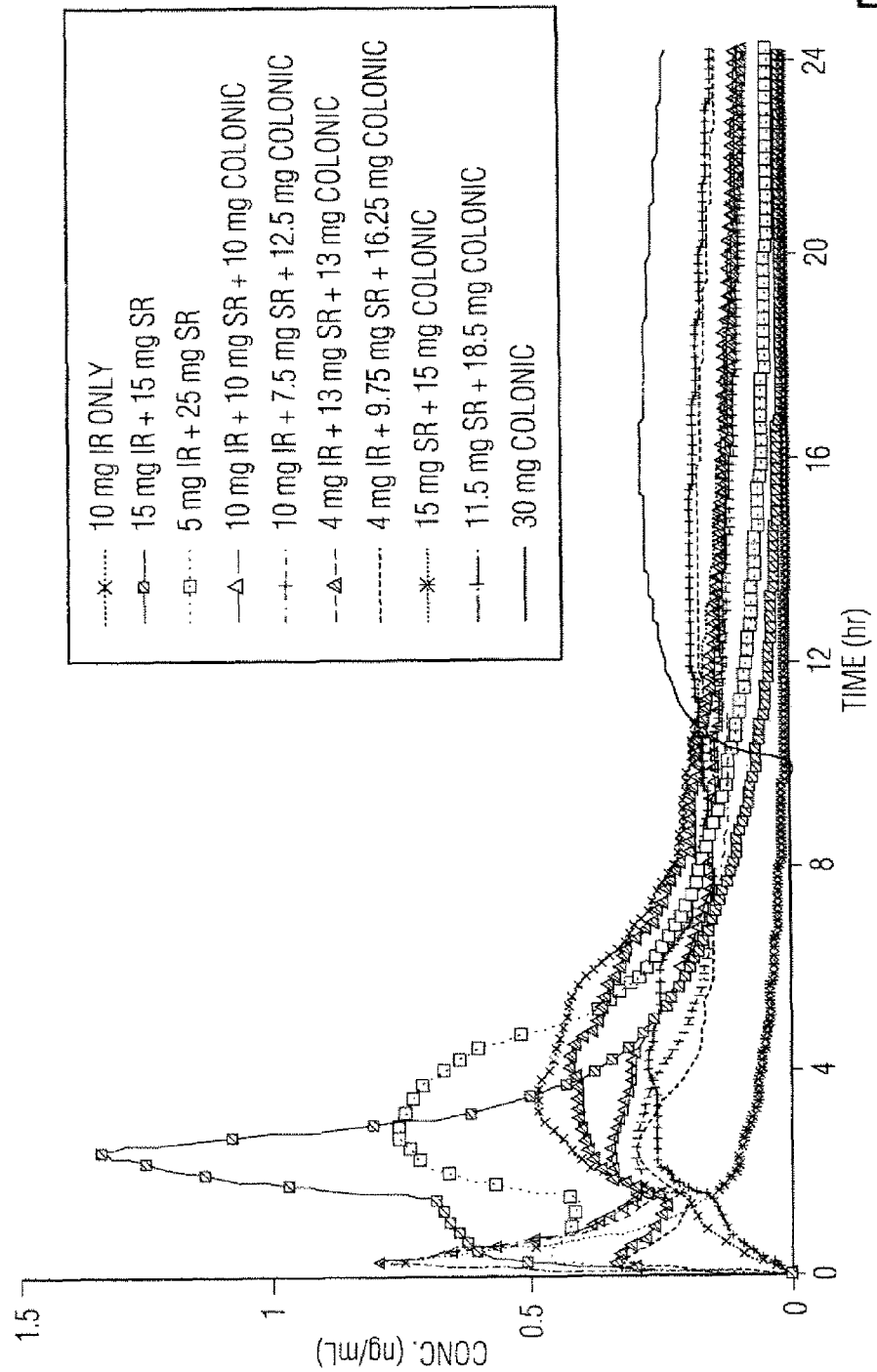

PHENYLEPHRINE PHARMACEUTICAL FORMULATIONS AND COMPOSITIONS FOR COLONIC ABSORPTION

REFERENCE TO RELATED APPLICATION

This application claims the benefit of priority to U.S. Provisional Patent Applications 60/810,021 filed Jun. 1, 2006 and 60/874,830 filed Dec. 14, 2006, the entire disclosure of each of the priority applications is hereby incorporated by reference.

BACKGROUND OF THE INVENTION

Phenylephrine and pharmaceutically acceptable salts thereof are recognized by those skilled in the art as safe and effective nasal decongestants for humans when administered at frequent intervals. Commercially-available formulations include nasal jelly, nasal drops, and nasal spray (i.e. Alconefrin® Nasal Drops or Neo-Synephrine® Nasal Jelly) as well as immediate release oral tablets or gelatin capsules (i.e. Sudafed PE™ or DayQuil® LiquiCaps). Due to a short half-life of the active phenylephrine species in plasma in vivo, phenylephrine and pharmaceutically acceptable salts thereof as currently formulated are commonly administered every four hours for the relief of nasal congestion.

Therefore there is an unmet need for less frequent delivery of phenylephrine for patient convenience and for sustained availability of the therapeutically active phenylephrine within a subject in need of such administration.

Less frequent administration results in improved patient compliance with appropriate dosing regimens. In addition, constant therapeutic plasma levels of active components can be more effective and even efficacious compared to the fluctuations seen when multiple doses of a conventional immediate release formulation are given, providing sustained effective levels and decreasing the severity and frequency of side effects from high peak plasma levels. Thus, formulations of phenylephrine that can be administered less frequently, for example, once every 8, 12, 16, 20, or 24 hours, are needed.

SUMMARY OF THE INVENTION

The present invention provides compositions and methods for efficient delivery of phenylephrine to provide improved and sustained bioavailability which provides efficacious phenylephrine in addition to improved convenience. The invention is based in part on the observation by the inventors that phenylephrine is efficiently absorbed from the colon and their appreciation that formulations which permit absorption from the colon will provide a larger proportion of phenylephrine remaining in a therapeutically active unconjugated form, in comparison to formulations permitting absorption from the upper areas of the gastrointestinal (GI) tract. The administration of a formulation providing for absorption from the colon has the additional advantage of sustaining plasma concentrations of active phenylephrine with a single bolus administration of the drug.

In one aspect, the invention provides pharmaceutical compositions suitable for oral administration comprising phenylephrine or a pharmaceutically acceptable salt thereof, wherein phenylephrine is made available for absorption from the colon. In one embodiment, the composition is a solid formulation comprising: a core comprising phenylephrine or a pharmaceutically acceptable salt thereof, and an erodible layer encapsulating the core, wherein the composition and the thickness of the erodible layer is such that the core is exposed when the composition enters the colon, or at around the time the composition reaches the colon.

In certain embodiments, the erodible layer comprises a polymer matrix. In other embodiments, the erodible layer is a coating. In one aspect, the erodible layer is a polymer matrix of certain composition and thickness so that the layer erodes over a certain amount of time. In another aspect, the erodible layer is a polymer matrix or a coating of certain composition which erodes upon encountering a certain environment. In certain embodiments, the erodible layer erodes at a certain pH. In other embodiments, the erodible layer comprises colon-specific substrates and erodes in the colon. In certain embodiments, the colon-specific substrate erodes in the presence of colon-specific enzymes and not while in transit through the upper digestive tract including the stomach and/or the small intestine. In another aspect, the invention provides pharmaceutical compositions suitable for oral administration comprising phenylephrine or a pharmaceutically acceptable salt thereof, wherein phenylephrine is made available for absorption from all pars of the GI tract including the duodenum, jejunum, ileum and colon. Certain embodiments of the invention are pharmaceutical compositions formulated as a single dosage form to deliver phenylephrine or a pharmaceutically acceptable salt thereof to a subject in need thereof, to provide a peak concentration of unmetabolized phenylephrine in plasma (of said subject) at about between 0.1 to 16 hours after ingestion of the composition and wherein the unmetabolized phenylephrine is maintained at a level greater than 0.1 ng/mL at about 6, 8, 12, and/or 24 hours after ingestion of the composition.

In certain embodiments, the erodible layer(s) and/or other component(s) of the composition other than the core comprise(s) phenylephrine or a pharmaceutically acceptable salt thereof. For example, in addition to the core comprising phenylephrine or a pharmaceutically acceptable salt thereof, phenylephrine is also dispersed in an erodible layer comprising a polymer matrix. The polymer matrix comprise(s) phenylephrine or a pharmaceutically acceptable salt thereof formulated for immediate release.

In certain embodiments, the composition further comprises an enteric coating and/or a top coating wherein the top coating functions to enhance the appearance or palatability of the formulation.

In one embodiment, the composition is a capsule formulation wherein phenylephrine or a pharmaceutically acceptable salt thereof is encased in a capsule which discharges its contents when the composition enters the colon, or at around the time the composition reaches the colon. In one embodiment, the composition is a capsule formulation wherein phenylephrine or a pharmaceutically acceptable salt thereof is encased in a capsule which discharges a portion of its contents when the composition enters the colon.

In one embodiment, the capsule formulation further comprises phenylephrine or a pharmaceutically acceptable salt thereof for immediate release and/or one or more additional therapeutic agent(s) for immediate or sustained release.

In yet another embodiment, the pharmaceutical composition of the invention is a casing with a release mechanism. Such structure is an insoluble casing housing a phenylephrine or a pharmaceutically acceptable salt thereof and a plug. The plug is removed after a predetermined lag time owing to swelling, erosion, or dissolution.

In still yet another embodiment, the pharmaceutical composition of the invention is formulated as a powder for constitution, an oral gel, an elixir, dispersible granules, a syrup, a suspension, or the like. In one embodiment, where the pharmaceutical composition of the invention is formulated as a powder for constitution, a suspension from such powder can be mixed immediately before use.

In one embodiment, the pharmaceutical composition of the invention is formulated such that it is suitable for pediatric use.

In one embodiments the pharmaceutical composition further comprises one or more addition therapeutic agent(s). Such agent or agents may be formulated for immediate release upon ingestion, for sustained-release, for release in the colon concomitantly with phenylephrine, or any combination thereof. The additional therapeutic agent may be a decongestant, an anti-pyretic, an anti-inflammatory, cough suppressant, expectorant, analgesic, or any other therapeutic agent or combinations of such agents useful to alleviate the symptoms of a cold, seasonal and other allergies, hay fever, or sinus problems, any of which may cause an increase in nasal discharge.

Another aspect of the invention is a method of treating the symptoms of cold, influenza, allergies, or non-allergic rhinitis in a subject in need thereof comprising administering a composition of the invention. In certain embodiments, the composition is administered every 8, 12, 16, 20, or 24 hours. In one preferred embodiment, the composition is administered every 12 hours.

Another aspect of the invention is methods of administering phenylephrine comprising delivering phenylephrine to the colon of a subject. Exemplary compositions useful for this method are described above. In certain embodiments, such method is a method wherein the maximal concentration of unconjugated phenylephrine in the plasma of the subject is reached between about 5 and about 24 hours after administration, and more preferably, between about 6 and about 12 hours after administration.

Certain embodiments of the invention are methods of maintaining sustained bioavailability of phenylephrine in a subject, comprising orally administering to the subject a composition comprising phenylephrine or a pharmaceutically acceptable salt thereof, wherein at least a portion of phenylephrine is absorbed from the colon, and wherein the concentration of unconjugated phenylephrine in the plasma of the subject is at least 0.1, 0.5, 1.0, or 2.5 ng/mL at 6 hours after administration of the composition. In particular embodiments, the concentration of unconjugated phenylephrine in the plasma of the subject is at least 0.1, 0.5, 1.0, or 2.5 ng/mL at 12 hours after administration of the composition. In particular embodiments, the concentration of unconjugated phenylephrine in the plasma of the subject is at least 0.1, 0.5, 1.0, or 2.5 ng/mL at 24 hours after administration of the composition.

Certain other embodiments of the invention are methods of administering phenylephrine to a subject, comprising orally administering a composition comprising phenylephrine or a pharmaceutically acceptable salt thereof, said composition delivering phenylephrine to the colon where phenylephrine is released in the colon and absorbed from the colon, thereby achieving a relative $AUC_{0-24}$, (determined as the percentage of the $AUC_{0-24}$ value of unconjugated phenylephrine relative at the $AUC_{0-24}$ value for the total (i.e. unconjugated+conjugated) phenylephrine in the plasma of the subject (see paragraph [0049] for exemplary methods of assaying)) of at least 1, 2, or 6%. In one embodiment, the percentage of the $AUC_{0-24}$ value of unconjugated phenylephrine relative to the $AUC_{0-24}$ value for the total phenylephrine in the plasma of the subject is at least about 1 to about 14%. In one embodiment, the percentage of the $AUC_{0-24}$ value of unconjugated phenylephrine relative to the $AUC_{0-24}$ value for the total phenylephrine in the plasma of the subject is at least about 2 to about 10%.

In yet another embodiment, the composition comprises a bi-layer tablet with an immediate release layer and an extended release layer.

As would be understood by one skilled in the art after reading the present specification, the erodible layer of the pharmaceutical compositions of the present invention provides a sustained or controlled release of phenylephrine providing a therapeutically effective amount to a subject for 8, 12, or 24 hours. In preferred embodiments, the present pharmaceutical compositions further comprise an additional amount of phenylephrine in an immediate release component affording an amount of phenylephrine upon administration to a subject.

In certain embodiments, it is preferable to have both an immediate release of phenylephrine which provides an initial burst followed by sustained release of phenylephrine in the colon over a period of 6, 8, 12, 16, or 24 hours. Likewise, in certain embodiments, it is preferable to have an immediate release of phenylephrine which provides an initial burst followed by sustained release of phenylephrine in the upper GI tract (i.e., the jejunum and the ileum) as well as in colon over a period of 6, 8, 12, 16, or 24 hours.

Other aspects of the invention provide methods of administering phenylephrine to a subject, wherein the pre-systemic modification of phenylephrine is minimized. Any of the methods described herein may be practiced using a pharmaceutical composition of the invention.

The present invention may be more fully understood by reference to the Figures, Detailed Description and Examples which follow.

BRIEF DESCRIPTION OF THE FIGURES

FIG. 1A is a schematic of an exemplary duration controlled erosion formulation. FIG. 1B is a schematic of a pellet core.

FIG. 2 is a schematic of an exemplary pH controlled erosion formulation.

FIG. 6 shows the mean plasma concentration profiles of total, as well as conjugated and unconjugated phenylephrine. In particular.

FIG. 7 shows simulated plasma concentration profiles for a 10 mg immediate release dose of phenylephrine as well as 30 mg phenylephrine dose scenarios (detailed in Table 17) covering the ranges detailed in Table 16.

DETAILED DESCRIPTION OF THE INVENTION

Definitions

Figure 3:
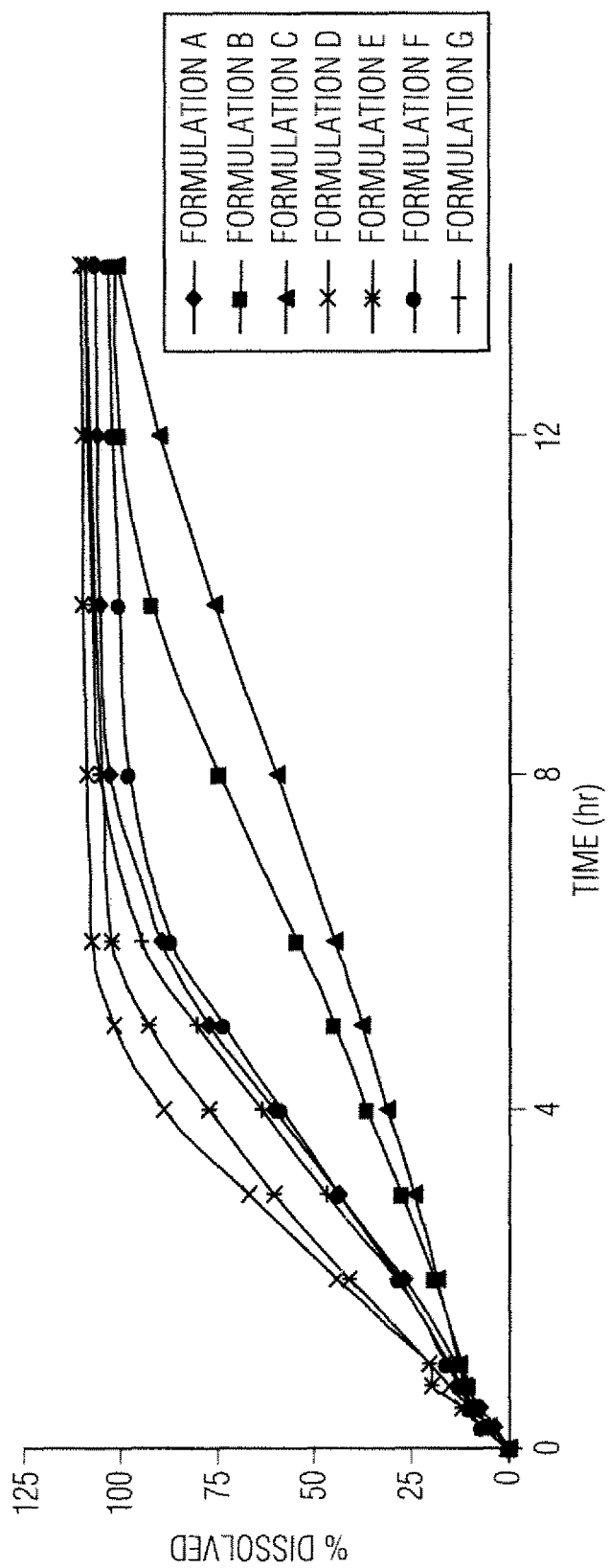
FIG. 3 shows the dissolution profile of Exemplary Formulations A-G.

As used herein a pharmaceutically acceptable salt of phenylephrine includes but is not limited to phenylephrine hydrochloride, phenylephrine bitartrate, phenylephrine tannate, etc. In one preferred embodiment, the pharmaceutically acceptable salt of phenylephrine is phenylephrine hydrochloride.

The term "unmetabolized phenylephrine" means phenylephrine that has not been chemically altered since entering the body of a subject except for the release of free base, i.e. phenylephrine that has not been conjugated by a sulotransferase or a UDP-glucuronosyltransferase. Unmetabolized phenylephrine exhibits therapeutic activity(ies). In this specification the term "unconjugated phenylephrine" is used interchangeably with "unmetabolized phenylephrine" and means the therapeutically active form of phenylephrine. "Unmetabolized phenylephrine" does not include phenylephrine that was at one time inactivated by conjugation but was later unconjugated and is not therapeutically active.

The term "pre-systemic modification" as used herein in connection with phenylephrine means modification of phenylephrine before phenylephrine is taken up into the bloodstream and thus into the plasma. Pre-systemic modification excludes modification of phenylephrine by the liver or within the bloodstream.

The term "environment in the colon" or "colonic environment" as used herein means the environment within the colon, in the alimentary canal.

The term "colon-specific" as used herein means characteristically, predominantly or exclusively seen in, related to or attributable to the colon but not other parts of the alimentary canal.

A "dosage" or "dose" as used herein means the amount of a pharmaceutical composition comprising therapeutically active agent(s) administered at a time. "Dosage" or "dose" includes administration of one or more units of pharmaceutical composition administered at the same time.

"AUC" as used herein means, for any given drug, the "area under the concentration-time curve" from dosing or activation of the drug to a time point, calculated by the trapezoidal rule. AUC is a parameter showing the cumulative plasma concentration of a drug over time, and is an indicator of the total amount and availability of a drug in the plasma. "$AUC_{0-t}$" is defined as AUC for any value of time (t) up to 24 hours. In a preferred embodiment, t is 24 hours (referred to herein as $AUC_{0-24}$). "$AUC_{0-\infty}$" is defined as calculated AUC extrapolated to infinity. $AUC_{0-\infty}$ is calculated as equal to $AUC_{0-t}+Ct/\lambda z$, wherein Ct is the concentration at 24 hours and $\lambda z$ is the terminal or elimination rate constant. Terminal or elimination rate constant $\lambda z$ is determined from the slope of the drug concentration-time curve using linear regression on terminal data points of the curve. "Relative $AUC_{0-t}$" is defined as the percentage of the $AUC_{0-t}$ value of unconjugated phenylephrine relative to the $AUC_{0-t}$ value for the total phenylephrine in the plasma of the subject from a dosing regimen. The present invention provides compositions and methods for efficient and effective delivery of phenylephrine providing improved bioavailability and convenience. Phenylephrine is effective when administered at frequent intervals in temporary relief of congestion and/or stuffiness caused by colds, seasonal and other allergies, hay fever, sinus problems or allergic and non-allergic rhinitis, which may cause an increase in nasal discharge. Currently, phenylephrine is available in nasal dosage forms and oral dosage forms for the treatment of these ailments. However, the oral dosage forms must be taken frequently, and exhibit sub-optimal effectiveness, due to a short half-life of active phenylephrine of approximately 2 hours in plasma caused by rapid metabolism of the active agent. Further, when administered orally, phenylephrine is rapidly absorbed from the GI tract but undergoes extensive intestinal mucosal pre-systemic modification, which results in the compound being converted to a form that is not active. The pre-systemic modification of phenylephrine mainly takes place during absorption from the upper intestinal tract, i.e., the jejunum and ileum, due to the activities of sulfotransferases and UDP-glucuronosyltransferases that are found there in greater number and quantities, in comparison with the lower tract, i.e., the colon. Upon entering the blood stream, phenylephrine is cleared from the plasma through the liver.

Without intending to be limited by any mechanism, the rapid and extensive conversion by the pre-systemic modification is thought, by the inventors, to reduce the effective concentration of phenylephrine in the plasma. In fact, the administration of phenylephrine every four hours in an immediate release dosage form, whether in tablet, capsule or solution, appears to have sub-optimal efficacy as a nasal decongestant.

The present invention is based in part on the observation that the absorption of phenylephrine from the lower intestinal tract, where sulfotransferases and UDP-glucuronosyltransferases are found in a smaller number and quantities, increases the bioavailability of phenylephrine by a factor of three compared to the bioavailability measured for an oral administration of phenylephrine in its immediate release form. An orally administered formulation is known to reach the ileocecal junction in a healthy adult on average in about 5 hours, and enter the colon on average in about 6 to 8 hours. In general, the range for an orally administered formulation to reach the colon is about 2 hours to about 8 hours. On average the residence time of ingested matter in the colon of a healthy adult is 12 to 24 hours. Further, due to the limited permeability of the colonic mucosal membrane and the residence time of ingested materials in the colon, a bolus administration of one or more additional therapeutic agent(s) that can be absorbed from the colon may result in sustained plasma levels of such agent absorbed from the colon. The greatly increased absorption of unconjugated phenylephrine from the colon far exceeds that which may be expected when compared to the colonic absorption of other active therapeutic agents which are known to be subject to similar pre-systemic modification.

Pharmaceutical Compositions

In one aspect, the invention provides pharmaceutical compositions suitable for oral administration comprising phenylephrine or a pharmaceutically acceptable salt thereof, wherein phenylephrine is made available for absorption for the colon. Certain embodiments of the invention are pharmaceutical compositions formulated as a single dosage form to deliver phenylephrine or a pharmaceutically acceptable salt thereof to a subject in need thereof such delivery resulting in detectable unmetabolized phenylephrine in plasma of a subject at about 5 hours after ingestion of the composition by said subject. In other embodiments, unmetabolized phenylephrine is detected at about 6, 8, 12, 16, 20, or 24 hours after ingestion of the composition by said subject. The presence of phenylephrine is detectable in plasma of a subject by methods used by one skilled in the art for assaying total phenylephrine and unconjugated phenylephrine in the plasma.

Exemplary methods for assaying total phenylephrine and unconjugated phenylephrine are described in the following: K. Gumbhir. An Investigation of Pharmacokinetics of Phenylephrine and its Metabolites in Humans, PhD Dissertation in Pharmaceutical Sciences, University of Missouri-Kansas City, Kansas City (1993); K. Gumbhir and W. D. Mason. Determination of m-hydroxymandelic acid, m-hydroxyphenylglycol and their conjugates in human plasma using liquid chromatography with electrochemical detection. *Journal of pharmaceutical and Biomedical Analysis* 12: 943-949 (1994); J. H. Hengstmannand J. Goronzy. Pharmacokinetics of $^3$H-Phenylephrine in Man. *European Journal of Clinical Pharmacology* 21: 335-341 (1982); V. Vumaand 1. Kanfer. High-performance liquid chromatographic determination of phenylephrine in human serum with coulometric detection, *Journal of Chromatography* 678: 245-252 (1996); M. Yamaguchi, H. Monji, I. Aoki, and T. Yashiki. High Performance liquid chromatographic determination of phenylephrine in human serum using coulometric switching flourescence detection. *Journal of Chromatography B*. 661: 93-99 (1994); A. Stockis, X. Deroubaix, B. Jeanbaptiste, R. Lins, A. M. Allemon, and H. Laufen. Relative Bioavailability of Carbinoxamine and Phenylephrine from a Retard Capsule after Single and Repeated Dose Administration in Healthy Subjects. *Arzneim.-Forsch./Drug Res*. 45: 1009-1012 (1995); A. Martinsson, S. Bevegård, and P. Hjemdahl. Analysis of Phenylephrine in Plasma: Initial Data About Concentration-Effect Relationship. *European Journal of Clinical Pharmacology* 30: 427-431 (1986); all of which are incorporated herein by reference. The amount of conjugated phenylephrine can be calculated by subtracting the amount of unconjugated phenylephrine assayed from the amount of total phenylephrine assayed.

Certain embodiments of the invention are pharmaceutical compositions formulated as a single dosage form to deliver phenylephrine or a pharmaceutically acceptable salt thereof to a subject in need thereof such that unmetabolized phenylephrine detectable in plasma of a subject for at least 4.5 hours after ingestion of the composition by said subject. In other embodiments, unmetabolized phenylephrine is detectable for at least about 5, 6, 8, 12, 16, 20, or 24 hours after ingestion of the composition.

In some embodiments, the composition is formulated to deliver at least a portion of phenylephrine to the colon of the subject. In other embodiments, in addition to delivery of a portion of phenylephrine to the colon of the subject, the composition is further formulated so that a sustained release of phenylephrine is achieved in the upper portion of the GI tract of the subject. In other embodiments in addition to delivery of a portion of phenylephrine to the colon of the subject, the composition is further formulated so that an immediate release of phenylephrine is achieved in the upper portion of the GI tract of the subject. In yet other embodiments in addition to delivery of a portion of phenylephrine to the colon of the subject, the composition is further formulated so that both an immediate release as well as a sustained release of phenylephrine is achieved in the upper portion of the GI of the subject. In all embodiments, by a portion is meant about 5-95% of the amount of phenylephrine or a pharmaceutically acceptable salt thereof administered. In specific embodiments, the portion is about 5, 10, 20, 25, 30, 50, 67, 75, 90, or 95% of the amount of phenylephrine or a pharmaceutically acceptable salt thereof administered. In certain embodiments, the portion is about ¼, ⅕, ¾, or 9/10 of the amount of phenylephrine or a pharmaceutically acceptable salt thereof administered. In other embodiments, the portion is about 17, 42, 45, 50, 54, or 61% of the amount of phenylephrine or a pharmaceutically acceptable salt thereof administered. Preferably, the portion is about 5-20% of the amount of phenylephrine or a pharmaceutically acceptable salt thereof administered. More preferably, the portion is about 10-15% of the amount of phenylephrine or a pharmaceutically acceptable salt thereof administered.

In one aspect, the invention provides pharmaceutical compositions suitable for oral administration comprising phenylephrine or a pharmaceutically acceptable salt thereof, wherein phenylephrine is made available for absorption from all parts of the GI tract including the duodenum, jejunum, ileum and colon. Certain embodiments of the invention are pharmaceutical compositions formulated as a single dosage form to deliver phenylephrine or a pharmaceutically acceptable salt thereof to a subject in need thereof, such delivery resulting in that the subject exhibits peak concentration of unmetabolized phenylephrine in plasma at about between 0.1 to 16 hours after ingestion of the composition and the unmetabolized phenylephrine is maintained at a level greater than 0.1 ng/mL at about 6, 8, 12, and/or 24 hours after ingestion of the composition. For example, in certain embodiments, the subject exhibits peak concentration of unmetabolized phenylephrine in plasma at about between 0.1 to 14 hours, 0.1 to 12 hours, 0.1 to 10 hours, 0.1 to 8 hours, 0.1 to 6 hours, 0.1 to 4 hours, 0.1 to 2 hours), after ingestion of the composition and the unmetabolized phenylephrine is maintained at a level greater than 0.1 ng/mL (e.g., 0.5 ng/ml, 1 ng/ml, or 2.5 ng/ml) at about 6, 8, 12, and/or 24 hours after ingestion of the composition. In one preferred embodiment, the subject exhibits peak concentration of unmetabolized phenylephrine in plasma at about between 0.75 to 2 hours after ingestion of the composition and the unmetabolized phenylephrine is maintained at a level greater than 0.1 ng/mL (e.g. 0.5 ng/ml, 1 ng/ml, or 2.5 ng/ml) at about 6, 8, 12, and/or 24 hours after ingestion of the composition.

In one preferred embodiment, the composition provides 12 hour sustained release of phenylephrine or a pharmaceutically acceptable salt thereof. In one embodiment, the composition is a solid formulation comprising a core for sustained release comprising phenylephrine or a pharmaceutically acceptable salt thereof and a coating layer over the core comprising phenylephrine or a pharmaceutically acceptable salt thereof for immediate or sustained release.

In one embodiment, the composition is formulated to deliver more than 40% of the total phenylephrine or a pharmaceutically acceptable salt thereof before entering the colon. In another embodiment, the composition is formulated to deliver at least a portion of the total phenylephrine or a pharmaceutically acceptable salt thereof, preferably more than 20%, immediately or within 1 hour after ingestion. More preferably, more than 40% of the total phenylephrine is delivered by sustained release to the upper portion of the GI tract of the subject before entering the colon. See, for example, Tables 16 and 17 dose scenario where about 33% is delivered to the colon, specifically Table 17 (dose scenario 10 mg IR+10 mg SR+10 mg colonic) and Table 18 (dose scenario 20 mg IR+20 mg SR+20 mg colonic). See also, preferred embodiment for 30 mg phenylephrine dose where about 17% is delivered to the colon, specifically 5 mg of 30 mg dose is delivered to the colon.

In another embodiment, the composition is formulated to deliver 25% of the total phenylephrine or a pharmaceutically acceptable salt thereof in an immediate release form and 75% of the total phenylephrine or a pharmaceutically acceptable salt thereof over 6-8 hours. See, for example, Tables 8 and 9. In one preferred embodiment, about 10-15% of the amount of phenylephrine or a pharmaceutically acceptable salt thereof administered is delivered to the colon.

In one embodiment, the composition comprises a core comprising phenylephrine or a pharmaceutically acceptable salt thereof; and one or more erodible layer(s) which degrade to expose and release phenylephrine or a pharmaceutically acceptable salt thereof for absorption in the colon. In certain embodiments, the erodible layer(s) comprises coating(s), polymer matric(es), and/or casing(s) encapsulating such core. In other embodiments, the erodible layer(s) comprises a matrix in which the core is embedded.

It is understood that additional components to facilitate and improve a pharmaceutical composition, such as one or more viscosity-modifying agents, stabilizing agents, and suspending agents, and buffers to maintain appropriate pH known in the art as pharmaceutically acceptable and conventionally used in a pharmaceutical composition are added as desired. Additional pharmaceutical excipients commonly accepted and used are found in, for example, Remington's Pharmaceutical Sciences (Gennaro, A., ed.), Mack Pub., 1990. Likewise, one or more sweeteners such as sucrose, saccharin, Sucralose etc. to improve palatability, one or more preservatives such as sodium benzoate, and/or food coloring are optionally added as desired. The pharmaceutical compositions of the invention may also comprise any one or more other additives conventionally used in the formulation of pharmaceutical compositions.

Methods of forming matrices and coatings with or without pharmaceutically active agents within such matrices and coatings are known in the art. For example, methods of forming controlled-release oral pharmaceutical formulations are described in Gupta and Robinson, "Oral controlled release delivery," Chapter 6 in Treatise on Controlled Drug Delivery, Editor A. Kydonieus, Dekker, N.Y., 1992; and in U.S. Pat. No. 7,163,696 (e.g., see column 3, line 22 to column 4 line 53), incorporated herein by reference.

Illustrative Exemplary Formulations or Compositions of the Present Invention

1) Time Dependent or Duration-Controlled Erosion Formulation

In a fasted healthy adult, the stomach empties every 45 to 80 minutes, and the transit time from mouth to the ileocecal junction is approximately 5 hours. Therefore a pharmaceutical composition comprising an erodible layer which erodes completely after about 5 to about 12 hours, preferably in about 6 to about 8 hours after ingestion will protect a core comprising phenylephrine until the target absorption site of the colon for phenylephrine's release is reached.

In one embodiment, the composition is a solid formulation comprising: a core comprising phenylephrine or a pharmaceutically acceptable salt thereof, and an erodible layer encapsulating the core and optionally comprising phenylephrine or a pharmaceutically acceptable salt thereof, wherein the composition and the thickness of the erodible layer is such that the core is exposed when the composition enters the colon, or at around the time the composition reaches the colonic junction.

In certain embodiments, wherein the erodible layer comprises phenylephrine or a pharmaceutically acceptable salt thereof, the erodible layer releases phenylephrine or a pharmaceutically acceptable salt thereof for absorption throughout the entire GI tract. For example, the inclusion of phenylephrine or a pharmaceutically acceptable salt thereof in one or more erodible layer(s) and/or an outer coating provides an immediate release and/or a sustained release of phenylephrine or a pharmaceutically acceptable salt thereof in the upper GI tract upon ingestion in addition to release of phenylephrine from the exposed core when the composition reaches the colon.

In certain embodiments, the composition further comprises an outer layer optionally containing phenylephrine or a pharmaceutically acceptable salt thereof in immediate release form in addition to phenylephrine or a pharmaceutically acceptable salt thereof in immediate release form in addition to phenylephrine or a pharmaceutically acceptable salt thereof for absorption in the colon. The outer coating may be an enteric coating. A scheme depicting the cross section of such formulation is represented in FIG. 1A. The formulation may further comprise a second outer coating or top coating to enhance the palatability of the formulation (not shown). The inclusion of phenylephrine in the erodible layer and/or an outer coating provide a sustained or an immediate release of phenylephrine in the upper gastrointestinal tract upon ingestion.

In one embodiment, the core is surrounded by the erodible layer(s) formulated as a conventional immediate release solid dosage form. In another embodiment, the core is an encapsulated liquid. In another embodiment, the core is a liquid-gel or a semi-solid. Upon exposure of the core to the environment in the colon, phenylephrine or a pharmaceutically acceptable salt thereof is released and delivered.

In another embodiment, the core is a pellet core (multiparticulate core). By "pellet core" it is meant that the core portion of the composition is not a uniform composition, but comprises smaller pellets comprising phenylephrine or a pharmaceutically acceptable salt thereof which pellets are embedded in a matrix material to form the core. Each pellet is optionally encased in an erodible layer to confer additional control over the release of phenylephrine ("erodible pellet coating"). In one embodiment, such erodible pellet coating comprises a pH-sensitive polymer. In another embodiment, the erodible pellet coating comprises a colon-specific polymer (see Section 3 below for suitable colon-specific polymers useful for erodible pellet coating). A pellet is spherical to elliptical, and has a dimension of 0.1 mm to 5 mm in the diameter or axis, preferably 0.2 to 2 mm, and more preferably 0.5 to 1.5 mm. A schematic showing such pellet core is shown as FIG. 1B. The overall structure of the pharmaceutical composition is as shown in FIG. 1A. Small pellets have been shown to have longer retention in the colon than unit dose tablets.

In one embodiment, the total dosage form comprises 1-150 mg (e.g., 1 mg, 2.5 mg, 5 mg, 7.5 mg, 10 mg, 12.5 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, or 150 mg) phenylephrine or a pharmaceutically acceptable salt thereof, which could be 0.2-90% w/w of the total dosage form.

In one embodiment, the pellet core comprises: 0.2-10% w/w of the core phenylephrine or a pharmaceutically acceptable salt thereof: 0-90% w/w microcrystalline cellulose such as Avicel® PH 101 (FMC BioPolymer, Philadelphia, Pa.); 0-80% agents for controlling the drug release rate, including but not limited to one or more of the following: a hydrophobic base such as glyceryl monostearate or glyceryl behenate available as Compitrol® 888 ATO (Gattefosse SA), a hydrophilic base such as hydroxypropyl methylcellulose (HPMC), polyvinyl alcohol, polyvinyl alcohol-polyethylene glycol graft copolymer (e.g., Kollicoat IR), hydroxyethyl cellulose (HEC), carboxymethylcellulose (CMC) or a salt of CMC (e.g., CMC sodium salt, CMC calcium salt); and 1-10% one or more disintegrants, such as crosspovidone or L-HPC.

Pellets are prepared by methods known in the art. In an exemplary method, pellets are prepared according to above formula, using distilled water as moistening liquid (up to 80% of formula dry weight). All components are mixed, moistened, and extruded through an extruder (such as an extruder available from Caleva Process Solutions Ltd., United Kingdom), and subsequently spheronized on a spheronizer (Caleva spheronizer). The wet pellets obtained are dried at appropriate temperature (tray dry or fluid-bed dry). The resulting pellets are elliptical to spherical and have a dimension of with 0.5 to 1.3 mm in diameter.

In certain embodiments, a pellet core comprises a matrix and pellets comprising phenylephrine or a pharmaceutically acceptable salt thereof. In certain embodiments, the matrix also comprises phenylephrine or a pharmaceutically acceptable salt thereof. In separate embodiments, only the pellets comprise phenylephrine or a pharmaceutically acceptable salt thereof. In another embodiment, only the matrix comprises phenylephrine or a pharmaceutically acceptable salt thereof.

In one embodiment, in addition to delivering phenylephrine or a pharmaceutically acceptable salt thereof in a sustained release form, the pellet core is formulated to deliver phenylephrine or a pharmaceutically acceptable salt thereof in an immediate release form. Similarly, in certain embodiments, in addition to delivering phenylephrine or a pharmaceutically acceptable salt thereof in a sustained release form, the pellet core is formulated to deliver one or more additional therapeutic agent(s) in an immediate release form and/or a sustained release form.

In one embodiment the core comprises individual pellets to which an erodible layer is applied. In one embodiment, multiple pellets are filled into capsules (e.g., gelatin capsules) or compressed into tablets to deliver the appropriate dose of phenylephrine.

In one embodiment, the erodible layer comprises a polymer such as Eudragit® L-30D, which resists erosion at pH below 5.6, Eudragit® L100-55, which resists erosion at pH below 5.5. Other suitable materials are hydroxypropyl methylcellulose phthalate (HPMCP), which is available in forms with threshold erosion pH of, for example, 4.5-4.8, 5.2, or 5.4. Cellulose acetate phthalate (CAP) may also be used.

In one embodiment, the total dosage form comprises 1 to 150 mg phenylephrine or a pharmaceutically acceptable salt thereof per dosage form, 0-90% (w/w relative to the dosage form) microcrystalline cellulose or other pharmaceutically acceptable diluent, and 0-5% w/w magnesium stearate or other pharmaceutically acceptable lubricant; the erodible layer comprises 20-40% w/w hydroxypropyl cellulose (HPC), 0-50% w/w carboxymethylcellulose (CMC) or a salt of CMC (e.g., CMC sodium salt, CMC calcium salt), 0-5% silicon dioxide, and 0-5% w/w magnesium stearate or other pharmaceutically acceptable lubricant. Such formulation may further comprise an erodible layer, comprising 1-150 mg phenylephrine or a pharmaceutically acceptable salt thereof per dosage form; and a top coating wherein the top coating functions to enhance the appearance of the formulation which comprises 1-10% w/w low molecular weight hydroxypropyl methylcellulose (HPMC), polyvinyl alcohol or Kollicoat IR, including a plasticizer up to 10% of its weight, and in case of an active coating, 1-30 mg phenylephrine or a pharmaceutically acceptable salt thereof per dosage form.

In one embodiment in addition to the core comprising phenylephrine or a pharmaceutically acceptable salt thereof, the composition further comprises phenylephrine or a pharmaceutically acceptable salt thereof for immediate release and/or one or more additional therapeutic agent(s) for either immediate or sustained release. In one embodiment, in addition to the core comprising phenylephrine or a pharmaceutically acceptable salt thereof the composition further comprises phenylephrine or a pharmaceutically acceptable salt thereof for immediate release and an antihistamine (e.g., loratadine or desloratadine) for immediate release. In one embodiment, the active agent(s) for immediate release are in a coating which erodes upon oral administration thereby exposing the inner layer(s) of the composition (e.g., the erodible layer).

In one embodiment, the composition further comprises a top coating, for example, to enhance the appearance or palatability of the formulation. In one embodiment, the top coating comprises a pharmaceutically acceptable coating polymer and a colorant. Examples of suitable pharmaceutically acceptable coating polymers include hydroxypropyl methylcellulose (HPMC), carboxymethylcellulose (CMC) or a salt of CMC (e.g. CMC sodium salt, CMC calcium salt), hydroxypropyl cellulose (HPC), polyvinyl alcohol, polyvinyl alcohol-polyethylene glycol grafted copolymer and pharmaceutically acceptable hydrophilic polymers.

In one embodiment, the top coating comprises 1 to 25 mg (0.02% w/w to 5% w/w) of polyvinyl alcohol and 0.1 to 5.0 mg (0.02% w/w to 1% w/w) Blue No. 1 colorant per dosage form.

In one embodiment, the total dosage form comprises: 1-150 mg phenylephrine or a pharmaceutically acceptable salt thereof, which could be 0.2-90% w/w of the total dosage form; 0-90% w/w microcrystalline cellulose such as Avicel® PH 102 (FMC BioPolymer, Philadelphia, Pa.) or any pharmaceutically acceptable tableting filler/diluents described in the Handbook of Pharmaceutical Excipients $4^{th}$ edition (Row, Shesheky and Walter, Pharmaceutical Press); 0-80% agents for controlling the drug release rate, including but not limited to one or more of the following: hydroxypropylcellulose (HPC), hydroxypropyl methyl cellulose (HPMC) (e.g., Methocel® K15M, Methocel® K100M, Methocel® K4M (Dow Corning)), carboxymethylcellulose (CMC) or a salt of CMC (e.g., CMC sodium salt, CMC calcium salt), and pharmaceutically acceptable hydrophilic polymers; and 0-15% magnesium stearate or other equivalent lubricating agent.

Due to the high water-solubility of phenylephrine, use of a hydrophilic polymer by itself results in rapid diffusion and release of active agent. To reduce the burst effect of the early release profile, the aforementioned pharmaceutically acceptable hydrophilic polymer can be combined with one or more hydrophobic polymer(s) (including but not limited to ethyl cellulose (Ethocel®)) or an acrylic acid copolymer.

In one embodiment, the preferred combination of polymers for sustained release forms a matrix with the active agent(s) (i.e., phenylephrine or a pharmaceutically acceptable salt thereof and optionally one or more additional therapeutic agent(s)) distributed within the matrix that provides a zero or near zero order release of active agent(s).

In one preferred embodiment, the combination of anionic carboxymethyl cellulose sodium salt and nonionic hydroxypropylcellulose provides a matrix with stronger crosslinking resulting in higher viscosity and a lower diffusion rate through the matrix for phenylephrine's particular solubility profile. The combination of hydroxypropylcellulose and carboxymethyl cellulose sodium salt allows for the design of a release profile that is specific and particular for phenylephrine so that it is completely eroded about 4 to 12 hours after ingestion. More preferably, the core is completely eroded about 4 to 8 hours after ingestion.

In one embodiment, the core comprises: phenylephrine or a pharmaceutically acceptable salt thereof, optionally microcrystalline cellulose, carboxymethylcellulose (CMC) or a salt thereof (e.g., sodium or calcium salt of CMC), hydroxypropylcellulose, optionally silicon dioxide colloidal, and magnesium stearate. For example, the core comprises the components and weight percent ranges detailed below in Table 1.

TABLE 1

| Components | Weight Percent Ranges |
| --- | --- |
| Phenylephrine Hydrochloride | 1–50 |
| Microcrystalline Cellulose NF | 0–60 |
| Carboxymethylcellulose Sodium or Calcium salt | 10–60 |
| Hydroxypropylcellulose | 20–40 |
| Silicon Dioxide Colloidal | 0–2 |
| Magnesium Stearate | 0.2–2 |

Exemplary Formulations A-G for extended release phenylephrine core are detailed below in Table 2.

TABLE 2

| Components | Exemplary Formulations A–G (mg/dose) | | | | | | |
| --- | --- | --- | --- | --- | --- | --- | --- |
| | A | B | C | D | E | F | G |
| Phenylephrine Hydrochloride | 20 | 20 | 20 | 20 | 20 | 20 | 20 |
| Hydroxypropyl Cellulose NF | 200 | 200 | 200 | 100 | 100 | 100 | 150 |
| Carboxymethylcellulose NF | 250 | 150 | 100 | 200 | 150 | 100 | 175 |
| Microcrystalline Cellulose NF | 20 | 120 | 170 | 170 | 220 | 270 | 145 |
| Colloidal Silicon Dioxide NF | 5 | 5 | 5 | 5 | 5 | 5 | 5 |
| Magnesium Stearate NF | 5 | 5 | 5 | 5 | 5 | 5 | 5 |
| Tablet Weight (mg) | 500 | 500 | 500 | 500 | 500 | 500 | 500 |

In one preferred embodiment, the total dosage form comprises the components and ranges (% w/w) detailed below in Table 3.

TABLE 3

| Components | Ranges % w/w |
| --- | --- |
| Phenylephrine Hydrochloride USP | 0.2–90 |
| Hydroxypropyl Cellulose NF 300–600 cPs at 10% | 5–90 |
| Hydroxypropyl Cellulose NF 150–300 cPs at 2% | 5–90 |
| Carboxymethylcellulose Sodium NF | 5–90 |
| Microcrystalline Cellulose NF | 1–80 |
| Magnesium Stearate NF | 0.1–2 |
| Polyvinyl Alcohol | 2–40 |

One particularly preferred embodiment of the extended release phenylephrine core is provided in Table 4.

TABLE 4

| Components | % w/w |
| --- | --- |
| Phenylephrine Hydrochloride USP | 4.5 |
| Hydroxypropyl Cellulose NF 300–600 cPs at 10% | 5 |
| Hydroxypropyl Cellulose NF 150–300 cPs at 2% | 5 |

TABLE 4-continued

| Components | % w/w |
| --- | --- |
| Carboxymeethylcellulose Sodium NF | 18 |
| Microcrystalline Cellulose NF | 66.5 |
| Magnesium Stearate NF | 1 |

In certain preferred embodiments, one or more rate controlling polymers are used instead of those detailed in Table 4. For example, suitable alternative hydrophilic polymers include hydroxypropylcellulose (HPC) having different viscosity, hydroxypropyl methyl cellulose (HPMC) having different viscosity, carboxymethylcellulose (CMC) sodium or calcium salt having different viscosity, and xanthan gum. Table 5 recites preferred ranges of exemplary alternative hydrophilic polymers.

TABLE 5

| Components | Ranges % w/w |
| --- | --- |
| Hydroxypropyl Cellulose NF 75–150 cps at 5% i.e. Klucel LXF or equivalent | 5–90 |
| Hydroxypropyl Cellulose NF 150–400 cps at 5% i.e. Klucel JXF or equivalent | 5–90 |
| Hydroxypropyl Cellulose NF 4000–6500 cps at 2% i.e. Klucel MXF or equivalent | 5–90 |
| Hydroxypropyl Cellulose NF 1500–3000 cps at 1% i.e. Klucel HXF or equivalent | 5–90 |
| Carboxymethylcellulose Sodium NF 25–3100 cps at 4% or equivalent | 5–90 |
| Carboxymethylcellulose Sodium NF 1500–3100 cps at 2% or equivalent | 5–90 |
| Carboxymethylcellulose Sodium NF 1000–2800 cps at 1% or equivalent | 5–90 |
| Carboxymethylcellulose Sodium NF 1500–3000 cps at 1% or equivalent | 5–90 |
| Hydroxypropyl methyl cellulose (HPMC) 100 cps at 2% i.e. Methocel K 100 | 1–80 |
| Hydroxypropyl methyl cellulose (HPMC) 4000 cps at 2% i.e. Methocel K4M | 1–80 |
| Poly(ethylene oxide) NF 30–1700 cps at 5% i.e. POLYOX ™ Water-Soluble Resins | 1–80 |
| Xanthan Gum NF | 1–80 |
| Polyvinyl Pyrrolidine 30–90 K molecular weight or equivalent | 1–80 |
| Acacia NF | 1–80 |
| Guar Gum NF | 1–50 |

Likewise, suitable alternative hydrophobic polymers include ethyl cellulose (Ethocel®) having various molecular weight, acrylic acid copolymers, pharmaceutical wax, and methyl cellulose having different viscosity. Table 6 recites preferred ranges of exemplary alternative hydrophobic polymers.

TABLE 6

| Components | Ranges % w/w |
| --- | --- |
| Hydroxypropyl Cellulose NF 75–150 cps at 5% i.e. Klucel LXF or equivalent | 5–90 |
| Hydroxypropyl Cellulose NF 150–400 cps at 5% i.e. Klucel JXF or equivalent | 5–90 |
| Ethyl cellulose, Ethocel ® NF | 1–50 |
| Glycerol monostearate NF | 1–50 |
| Methyl cellulose, Methocel ® | 1–50 |
| Acrylic Acid Copolymer, Eudragit | 1–50 |
| Paraffin NF | 1–50 |

TABLE 6-continued

| Components | Ranges % w/w |
|---|---|
| Hydrogenated vegetable Oil NF | 1–50 |
| Hydrogenated Castor Oil NF | 1–50 |
| Carnauba Wax NF | 1–50 |
| White Wax NF | 1–50 |

In one embodiment, the composition further comprises 1 to 25 mg phenylephrine or a pharmaceutically acceptable salt thereof in an immediate release form, 0-90% (w/w relative to the dosage form) of one or more pharmaceutical diluent(s) or other pharmaceutically acceptable tableting agent(s). Examples of such tableting agents are microcrystalline cellulose, starch, pre-gelatinized starch, lactose or other tableting sugars, calcium phosphate or any other pharmaceutically suitable tableting excipients.

In one embodiment, the composition further comprises an erodible coating comprising 1 to 25 mg phenylephrine or a pharmaceutically acceptable salt in an immediate release form, 2-20% (w/w relative to the dosage form) polyvinyl alcohol or other pharmaceutically acceptable coating agent. In another embodiment, the composition further comprises an erodible coating comprising 1 to 25 mg phenylephrine or a pharmaceutically acceptable salt in an immediate release form, 4-8% (w/w relative to the dosage form) polyvinyl alcohol or other pharmaceutically acceptable coating agent. Examples of pharmaceutically acceptable coating agents are hydroxypropyl methylcellulose (HPMC), polyvinyl alcohol, Kollicoat IR, carboxymethylcellulose (CMC) or a salt of CMC (e.g., CMC sodium salt, CMC calcium salt), hydroxypropyl cellulose (HPC), or any other pharmaceutically suitable hydrophilic polymers. In one preferred embodiment, the pharmaceutically acceptable coating agent is based on polyvinyl alcohol (e.g., Opadry™ II 85 series, preferably 18422; polyvinyl alcohol-polyethylene glycol graft copolymer (e.g., Kollicoat IR)).

In a preferred embodiment, the immediate release portion comprises phenylephrine or a pharmaceutically acceptable salt thereof as well as a polyvinyl alcohol. Such immediate release formulations and methods of making the same are described in U.S. Provisional Patent Application No. 60/941, 577 filed on Jun. 1, 2007 entitled "Coatings for applying substances onto substrate carrier," hereby incorporated by reference.

In one embodiment, the composition further comprises one or more additional therapeutic agent(s) formulated for immediate and/or sustained release. In one preferred embodiment, the one or more additional therapeutic agent(s) is an antihistamine, preferably, loratadine or desloratadine. Accordingly, in one embodiment, the composition comprises the following sustained release portion and immediate release portion detailed below in Table 7.

TABLE 7

| Sustained release core Components | Weight Percent Ranges (w/w) of dosage form |
|---|---|
| Phenylephrine Hydrochloride | 1–50 |
| Microcrystallinne Cellulose NF | 0–60 |
| Carboxymethylcellulose Sodium or Calcium salt | 10–60 |
| Hydroxypropylcellulose | 20–40 |
| Silicon Dioxide Colloidal | 0–2 |
| Magnesium Stearate | 0.2–2 |

| Seal coating (Optional) Components | Exemplary Formulation (mg/tablet) | Weight Percentages in solution (w/w) |
|---|---|---|
| Polyethylene Glycol 3350 | 1.67 | 2.28% |
| Hydroxypropyl methyl cellulose (HPMC) 5 cps at 2% (e.g., Methocel E-5 Premium LV) or a polyvinyl alcohol based polymer (e.g., Opadry ™ II 85 series, preferably 18422; polyvinyl alcohol-polyethylene glycol graft copolymer (e.g., Kollicoat IR)) | 8.33 | 11.36% |

| Immediate release-erodible Components | Exemplary Formulation (mg/tablet) | Weight Percentages in solution (w/w) |
|---|---|---|
| Polyethylene Glycol 3350 | 3.65 | 1.35% |
| Hydroxypropyl methyl cellulose (HPMC) 5 cps at 2% (e.g., Methocel E-5 Premium LV) or a polyvinyl alcohol based polymer (e.g., Opadry ™ II 85 series, preferably 18422; polyvinyl alcohol-polyethylene glycol graft copolymer (e.g., Kollicoat IR)) | 14.6 | 5.38 |
| Loratadine (optional) | 5 | 1.84 |
| Opaspray Blue K-1-4108 (optional dye) | 8.2 | 3.02 |
| Phenylephrine HCl 150 mesh | 8–12 | 3.1–4.22 |
| Immediate release coating total | 39.45–43.45 | 13.28–17.28 |

| Top coating (optional) Components | Exemplary Formulation (mg/tablet) | Weight Percentages in solution (w/w) |
|---|---|---|
| Polyethylene Glycol 400 | 0.75 | 2.27 |
| Hydroxypropyl methyl cellulose (HPMC) 5 cps at 2% (e.g., Methocel E-5 Premium LV) or a polyvinyl alcohol based polymer (e.g., Opadry ™ II 85 series, preferably 18422; polyvinyl alcohol-polyethylene glycol graft copolymer (e.g., Kollicoat IR)) | 3.75 | 11.37 |

In another preferred embodiment, the composition comprises the following sustained release portion and immediate release portion detailed below in Table 8.

TABLE 8

| | Weight Percent Ranges (w/w) of dosage form | Exemplary Formulation (mg/tablet) |
|---|---|---|
| Extended release core Components | | |
| Phenylephrine Hydrochloride USP | 4–5 | 22.5 |
| Hydroxypropyl Cellulose NF 300–600 cPs at 10% | 4–5 | 25 |
| Hydroxypropyl Cellulose NF 150–300 cPs at 2% | 4–5 | 25 |

TABLE 8-continued

| | Weight Percent Ranges (w/w) of dosage form | Exemplary Formulation (mg/tablet) |
|---|---|---|
| Carboxymethylcellulose Sodium NF | 16–17 | 90 |
| Microcrystalline Cellulose NF | 60–62 | 332.5 |
| Magnesium Stearate NF | 0.9–1 | 5 |
| Immediate release erodible layer coating Components | | |
| Loratadine, micronized (optional) | 0.9–1 | 5 |
| Phenylephrine Hydroxhloride | 1–2 | 7.5 |
| Polyvinyl alcvohol based polymer (e.g., Opadry ™ II 85 series (e.g., 18422 (White)) or polyvinyl alcohol-polyethylene glycol graft copolymer (e.g., Kollicoat IR) | 6–10 | 36–54 |

In any of the preceding embodiments, the core optionally comprises a penetration enhancer. Examples of penetration enhancers are salicylates such as sodium salicylate, 3-methoxysalicylate, 5-methoxysalicylate and homovanilate; bile acids such as taurocholic, tauorodeoxycholic, deoxycholie, cholic, glycholic, lithocholate, chenodeoxycholic, ursodeoxycliolic, ursocholic, dehydrocholic, fusidic, etc.; non-ionic surfactants such as polyoxyethylene ethers (e.g. Brij 36T®, Brij 52®, Brij 56®, Brij 76®, Brij 96®, Texaphor® A6, Texaphor® A14, Texaphor A60 etc.), p-t-octyl phenol polyoxyethylenes (Triton® X-45, Triton® X-100, Triton® X-114, Triton® X-305 etc.) nonylphenoxypoloxyethylenes (e.g. Igepal® CO series), polyoxyethylene sorbitan esters (e.g. Tween®-20 Tween®-80 etc.); anionic surfactants such as dioctyl sodium sulfosuccinate; lyso-phospholipids such as lysolecithin and lysophosphatidylethanolamine; acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N'-acylglycine etc.; water soluble phospholipids; medium-chain glycerides which are mixtures of mono-, di- and triglycerides comprising medium-chain-length fatty acids (caprylic, capric and lauric acids); ethylenediaminetetraacetic acid (EDTA); cationic surfactants such as cetylpyridinium chloride; fatty acid derivatives of polyethylene glycol such as Labrasol®, Labrafac®, etc.; and alkylsaccharides such as lauryl maltoside, lauroyl sucrose, myristoyl sucrose, and palmitoyl sucrose.

In yet other embodiments, the pharmaceutical composition of the invention is a casing with a release mechanism. Such structure is an insoluble casing housing a phenylephrine or a pharmaceutically acceptable salt thereof and a plug. The plug is removed after a predetermined lag time owing to swelling, erosion, or dissolution. In certain embodiments, the casing is typically a capsule. A commercially available capsule system is Pulsincap® (Scherer DDS, Ltd, Clydebank, Glasgow, UK). In this system, an insoluble capsule is sealed with a hydrogel plug, which hydrates in the GI fluid in a time-dependent manner, and swells to an extent that it is expelled from the capsule body, thus releasing its content. In one embodiment, the plug is expelled about 5 to 12 hours after ingestion. In a preferred embodiment, the plug is expelled about 6 to 8 hours after ingestion. In a particular embodiment, the easing comprises phenylephrine or a pharmaceutically acceptable salt thereof and one or more additional therapeutic agent(s) as well as excipients known in the art. An exemplary embodiment comprises a capsule comprising 1 to 150 mg phenylephrine, 0-90% (w/w relative to the dosage form) microcrystalline cellulose or other pharmaceutically acceptable diluent, and 0-5% w/w magnesium stearate or other pharmaceutically acceptable lubricant. In another embodiment, the capsule comprises pellets as described above, which pellets comprise phenylephrine or a pharmaceutically acceptable salt thereof, and one or more additional therapeutic agent(s) as well as excipients known in the art.

In one embodiment, an insoluble casing is capped by a cap which dissolves immediately upon oral administration, exposing a polymer plug optionally comprising phenylephrine or a pharmaceutically acceptable salt thereof for immediate release. The polymer plug is constructed of an erodible polymer, which plug has an appropriate thickness and erodes over a desired duration. Examples of such hydrophilic polymers are hydroxypropyl methylcellulose (HPMC), polyvinyl alcohol, Kollicoat IR, carboxy ethylcellulose (CMC) or a salt of CMC (e.g., CMC sodium salt, CMC calcium salt), hydroxypropyl cellulose (HPC), or any other pharmaceutically suitable hydrophilic polymers. The plug erodes over about 5 to 12 hours from ingestion, more preferably over about 6 to 8 hours from ingestion.

2) pH Dependent Erosion Controlled Formulation

In another embodiment, the composition is a solid formulation wherein phenylephrine or a pharmaceutically acceptable salt thereof is released under a condition that exists characteristically, predominantly or exclusively in the colon (colon-specific condition) and not while in transit through the upper digestive tract including the stomach and/or the small intestines. A pH-sensitive polymer applied at an appropriate thickness may be used to prevent release of the phenylephrine until the product has reached the colon. By "pH-sensitive," it is meant that a polymer disintegrates above or below a certain pH value or within a certain range of pH values. In preferred embodiments, the pH dependent erodible layer can have an enhanced thickness to control the duration of erosion and/or include the presence of one or more enzymes specific to or prevalent in the colon to further continue erosion.

Along the GI tract, the pH within a fasted stomach ranges from 1.5 to 3, and a fed stomach pH 2-5. In the small intestine, the pH within a fasted duodenum is approximately 6.1, while after ingestion of food, it drops to about 5.4. The ileum has a pH of about 7 to 8. In the colon, the pH within the cecum and colon ranges from 5.5 to 7. This neutral pH condition is sustained into the rectum. See Patel et at, *Drug Delivery Technol,* 6(7):62-71 (July/August 2006).

In one embodiment, the composition of the invention comprises, a core comprising phenylephrine or a pharmaceutically acceptable salt thereof and an erodible colon-specific layer encapsulating the core and degradable at the colonic pH of about 5.5 or above, an optional layer comprising phenylephrine for immediate release in the upper tract of the intestines, and an optional second coating (e.g., an enteric coating). Preferably, the colon specific layer is degradable at the colonic pH of about 5.7 to about 6.8. The formulation may further comprise a top coating to enhance the palatability of the formulation which top coating optionally may also be an active coating comprising phenylephrine for immediate release. Such an embodiment delivers from one to three pulsed releases of phenylephrine at different regions of the GI tract. A scheme depicting the cross section of such formulation is represented in FIG. 2. The core is formulated as a conventional immediate release solid dosage for, which allows a bolus delivery of phenylephrine upon exposure of the core to the colonic environment. The colon-specific layer may further comprise an additional enteric coating for protection from the low pH of the stomach. In such embodiment, the core and any optional additional layer(s) is encapsulated by an enteric coating comprising a composition that resists degradation under the prevailing pH of the stomach. A commonly used enteric coating resists degradation in the stomach where the pH is below 2. An example of such enteric coating comprises hydroxypropyl methylcellulose phthalate, polyvinyl acetate phthalate or methacrylic acid copolymers. Commercially available preparations include Eudragit® L-100, which dissolves at pH 6.0, and S-100, which dissolves at pH 7.0, used as a mixture. (Rohm Pharma GmbH, Germany). Another example of polymers suitable for use as an enteric coating is hypromellose acetate succinate (HPMCAS). See, for example, Tanno et al., *Drug Dev Ind Pharm,* 30(1):9-17 (January 2004). HPMCAS is commercially available in different grades such as HPMCAS MF (threshold pH 6.0), or HPMCAS HF (threshold pH 6.8) (Shin-Etsu Chemical Co. Ltd., Tokyo, Japan) and may be used as a combination of both these polymers. The coating is formulated with one or more appropriate plasticizers. The methods of preparing the coating as desired are known in the art and described more fully in the product literature from the manufacturers of these polymers.

In an exemplary formulation, the total dosage form comprises 1 to 150 mg phenylephrine or a pharmaceutically acceptable salt thereof per dosage form, 0-90% (w/w relative to the dosage form) microcrystalline cellulose or other pharmaceutically acceptable diluent, and 0-5% w/w magnesium stearate or other pharmaceutically acceptable lubricant; the colon-specific layer comprises Eudragit L-100 and if an additional enteric coating is advantageous, such enteric coating up to 10% w/w of the total dosage form (5-35% of weight gain by the addition of matrices and coatings), and comprises hydroxypropyl methylcellulose phthalate dissolvable in the media above pH 6.8. Further, the composition optionally comprises a top coating comprising 1-10% w/w low molecular weight hydroxypropyl methylcellulose, polyvinyl alcohol, or Kollicoat IR, including a plasticizer up to 10% of its weight, and in case of an active coating, 1-30 mg phenylephrine or a pharmaceutically acceptable salt thereof per dosage form.

In another embodiment, the core of a pharmaceutical composition of the invention is a pellet core and comprises pellets comprising phenylephrine or a pharmaceutically acceptable salt thereof. Pellet cores are described above and exemplified in FIG. 1B. In another embodiment the core comprises individual pellets comprising phenylephrine or a pharmaceutically acceptable salt thereof; to which pellets the colon-specific layer is applied. Multiple pellets are filled into gelatin capsules or compressed into tablets to deliver the appropriate dose of phenylephrine. As in other embodiments multiple layers may be added to the pellets to provide additional pulses of drug release in different regions of the GI tract.

3) Colon-Specific Erosion Formulation

In other embodiments, the composition comprises a core comprising phenylephrine or a pharmaceutically acceptable salt thereof and a colon-specific layer degradable by one or more enzymes specific to or prevalent in the colon. Such enzyme is herein referred to as "colon-specific enzyme." The enzymes may be produced by mammalian cells of the colon, or may be excreted by the bacterial population of the colonic microflora. An example of such enzyme is azoreductase, which cleaves an aromatic azo bond. A gel based on N,N-dimethylacrylamide, N-t-butylacrylamide, and acrylic acid cross-linked with azoaromatic compounds of varying length may be used to provide an erodible layer degradable by such colon-specific enzyme. Brondsted et al, *Pharmaceutical Res,* 9(12) 1540-1545 (December 1992). Urethane-based analogues comprising an azo aromatic linkage are also useful to provide an erodible layer in practice of this invention. Additional enzymes found in the colon are nitroreductase, N-oxide reductase, sulfoxide reductase, hydrogenase, esterases and amidases, glucosidase, glucuronidase, sulfatase, and others. Examples of such colon-specific erodible layers include but are not limited to layers comprising a polysaccharide, such as chitosan, a natural polymer obtained by the hydrolysis of chitin, shellac, ad certain forms of starch such as pea starch. Combinations of pectin, chitosan, and hydroxypropyl methylcellulose, polyvinyl alcohol, or Kollicoat IR, are also useful to practice this embodiment of the invention. Amylose-ethylcellulose film can also be used. See Siew et al., *AAPS PharmSciTech,* 1(3): article 22 (2000); Tuleu et at, *Alimentary Pharmacol Therapeut,* 16(10): 1771 (October 2002); Chaubal, *Drug Delivery Technol,* Article 131. Guar gum, methacrylated inulin, and dextran acetate are a few other examples. The core comprising phenylephrine is protected from the stomach acid by an enteric coating when necessary, such as when a polysaccharide based coating is used.

In another embodiment, a core of a pharmaceutical composition of the invention is a pellet core and comprises pellets comprising phenylephrine or a pharmaceutically acceptable salt thereof. Pellet cores are described above and exemplified in FIG. 1B. In another embodiment the core comprises individual pellets comprising phenylephrine or a pharmaceutically acceptable salt thereof, to which pellets the colon-specific layer is applied. Multiple pellets are filled into gelatin capsules or compressed into tablets to deliver the appropriate dose of phenylephrine. As in other embodiments multiple layers may be added to the pellets to provide additional pulses of drug release in different regions of the GI tract.

In yet another embodiment, the formulations of the invention suitable for colon-targeting compositions of phenylephrine or a pharmaceutically acceptable salt thereof comprise a combination of two or more duration-controlled, pH-controlled, or colon-enzyme controlled erodible layers for a more fine-tuned control. See, above for details and generally Cheng et al., *World J Gastroenterol,* 10(12) 1769-1774 (2004); Asghar et al, *J Pharm Pharmaceut Sci,* (3):327-338 (2006); Li et al., *AAPS PharmSciTech,* 3(4):article 33 (2002).

For example, in addition to the core comprising phenylephrine or a pharmaceutically acceptable salt thereof preferably an amount of phenylephrine is also dispersed in a coating layer comprising a polymer composition. The coating layer comprising a portion of phenylephrine releases its phenylephrine content immediately upon ingestion to aid in achieving the peak plasma concentration of unmetabolized or unconjugated phenylephrine form.

4) Combination Formulations with One or More Additional Therapeutic Agent(s)

In another embodiment of the invention, the pharmaceutical composition further comprises one or more additional therapeutic agent(s). Such agent or agents may be formulated for immediate release upon ingestion, for sustained-release, for release in the colon, or any combination thereof.

In certain embodiments, one or more additional therapeutic agent(s) are added to a formulation in any of the coatings or layers described above in any combination as suitable. In one embodiment, the pharmaceutical composition is a duration-controlled erosion formulation having a structure depicted in FIG. 1. In one embodiment, the core further comprises one or more additional therapeutic agent(s) for release in the upper GI tract and/or the colon concurrently with phenylephrine. In a particular embodiment, one or more additional therapeutic agent(s) are formulated within pellets of a pellet core. In another embodiment, one or more additional therapeutic agent(s) are formulated in the matrix surrounding the pellets in a pellet core. In one embodiment, one or more additional therapeutic agent(s) are formulated within pellets of a pellet core as well as within the matrix surrounding the pellets in a pellet core. In another embodiment, an erodible layer comprises one or more additional therapeutic agent(s) for immediate release in the small intestines. In another embodiment, one or more additional therapeutic agent(s) are formulated into the erodible layer or sustained release. In another embodiment, an active top coating comprises one or more additional therapeutic agent(s) for immediate release after ingestion. In certain embodiments, the pharmaceutical compositions of the invention comprise one or more additional therapeutic agent(s) in one or more of the core or any of the layers or coatings as described above.

In another embodiment, one or more additional therapeutic agent(s) are added to a pH-dependent or colon-specific erosion formulation having a structure depicted in FIG. 2. Similarly to the above description, any core or layer of the formulation may comprise one or more additional therapeutic agent(s) for a desired timing of release.

The additional therapeutic agent may be a decongestant including anti-histamine, an anti-pyretic, a non-steroidal anti-inflammatory, or any other therapeutic agent or combination of two or more of such agents to assist alleviation of the symptoms of a cold, a seasonal or non-seasonal allergy, hay fever, or sinus problems. In a preferred embodiment, the pharmaceutical compositions include an antihistamine.

Antihistamines can be of H1 or H2 antagonists or other types of histamine release inhibitors. The H1 antagonists can be sedating or non-sedating, such as diphenhydramine, chlorpheniramine, tripelennamine, promethazine, clemastine, doxylamine, astemizole, terfenadine, and loratadine, among others. Examples of H2 antagonists include, but are not limited to, cimetidine, famotidine, nizatidine, and ranitidine. Examples of histamine-release inhibitors include cromolyn. Long-acting antihistamines selected from one or more of the group consisting of loratadine, desloratadine, azatidine, fexofenadine, terfenadine, cetirizine, astemizole, and levocabastine, or their pharmaceutically acceptable salts are suitable for the pharmaceutical compositions of the invention.

Preferred antihistamines include loratadine and desloratadine. Loratadine is disclosed in U.S. Pat. No. 4,282,233 as a non-sedating antihistamine useful, for example, in alleviation of seasonal allergic rhinitis symptoms such as sneezing and itching. The active metabolite of loratadine is desloratadine, which has a half-life (tea) of approximately 15 to 19 hours. U.S. Pat. No. 5,595,997 discloses methods and compositions for treating seasonal allergic rhinitis symptoms using desloratadine. Loratadine and desloratadine are available in the form of conventional tablets that release the active agent in a conventional manner. An exemplary formulation releases loratadine by the processes of disintegration and dissolution such that loratadine begins to elicit its antihistaminic effect within 1 to 3 hours and the effect lasts in excess of 24 hours. Due to the long half life of loratadine compared to phenylephrine, the loratadine in the formulation according to the present invention is preferably available for immediate release. For example, loratadine or desloratadine may be present in solution in the carrier liquid of a liquid core or incorporated into the top coating of the product.

Other antihistamines are also useful for the practice of the instant invention. Azatadine is disclosed in Belgian Patent No. 647,043 and in corresponding U.S. Pat. Nos. 3,326,924 and 3,419,565. The elimination half-life is reported to be 9-12 hours. Terfenadine and fexofenadine are disclosed in U.S. Pat. No. 3,878,217 and have a duration of action of 12 to 24 hours, and greater than 24 hours, respectively. Cetirizine is disclosed in U.S. Pat. No. 4,525,358 and is reported to have a duration of action of 12 to 24 hours. Astemizole is disclosed in U.S. Pat. No. 4,219,559 and is reported to have a duration of action greater than 24 hours. Levocabastine is disclosed in U.S. Pat. No. 4,369,184 and is reported to have a duration of action of 16 to 24 hours.

The dosage of antihistamine such as loratadine or desloratadine may be present in different concentrations such as 1-20 mg; preferably 2.5 mg, 5 mg, or 10 mg.

Suitable anti-inflammatory and/or antipyretic agents useful for the present compositions may be: a non-steroidal anti-inflammatory (NSAIDs), aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ÿ-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof, and other analgesics, such as acetaminophen. The dosage of analgesic and/or antipyretic such as aspirin, acetaminophen, etc. will be known to those skilled in the art and can be in the range of 80 mg to 250 mg. The dosage of NSAID will be known to those skilled in the art and can be in the range of 80 mg to 500 mg.

Exemplary formulations of phenylephrine in combination with loratadine are described below.

One preferred embodiment is a formulation comprising sustained release of phenylephrine or a pharmaceutically acceptable salt thereof and immediate release of phenylephrine or a pharmaceutically acceptable salt thereof and loratadine. For example, the formulation comprises an extended release tablet core wherein the components comprise 22.5 mg phenylephrine hydrochloride and an immediate release active coating encapsulating the core wherein the components comprise 7.5 mg phenylephrine hydrochloride and 5 mg loratadine (Table 9). In addition to 22.5 mg phenylephrine hydrochloride, the tablet core components comprise one or more of the following: hydroxypropyl cellulose, carboxymethylcellulose sodium, microcrystalline cellulose and magnesium stearate. The immediate release coating components further comprise polyvinyl alcohol as a film forming polymer matrix with loratadine and phenylephrine or pharmaceutically acceptable phenylephrine salt. A top coating may further be applied as a seal coating wherein the components comprise polyvinyl alcohol and may also comprise colorant for appearances.

TABLE 9

| Extended release core Components | Weight Percent Ranges (w/w) of dosage form | Exemplary Formulation (mg/tablet) |
|---|---|---|
| Phenylephrine Hydrochloride USP | 4–5 | 22.5 |
| Hydroxypropyl Cellulose NF 300–600 cPs at 10% | 4–5 | 25 |
| Hydroxypropyl Cellulose NF 150–300 cPs at 2% | 4–5 | 25 |
| Carboxymeethylcellulose Sodium NF | 16–17 | 90 |
| Microcrystalline Cellulose NF | 59–61 | 332.5 |
| Magnesium Stearate NF | 0.9–1 | 5 |

| Immediate release erodible layer coating Components | Weight Percent Ranges (w/w) of dosage form | Exemplary Formulation (mg/tablet) |
|---|---|---|
| Loratadine, micronized | 0.9–1 | 5 |
| Phenylephrine Hydrochloride | 1–2 | 7.5 |
| Polyvinyl alcohol based polymer (e.g., Opadry™ II 85F series (e.g., 18422 (White)) or polyvinyl alcohol-polyethylene gglycol graft copolymer (e.g., Kollicoat IR) | 6–10 | 36–54 |

| Top coating (optional) Components | Weight Percent Ranges (w/w) of dosage form | mg/tablet |
|---|---|---|
| Polyvinyl alcohol based polymer (e.g., Opadry™ II 85F series (e.g., 18422 (White)) or polyvinyl alcohol-polyethylene glycol graft copolymer (e.g., Kollicoat IR) | 2–3 | 15 |

TABLE 9-continued

| Imprinting (optional) Components | Weight Percent Ranges (w/w) of dosage fform | mg/tablet |
|---|---|---|
| Opacode$^D$ WB ND-78-10526 (Blue) | >0.1 | Traceamount |

The preferred manufacturing process for one embodiment comprising a tablet formulation such as exemplified in Table 9, is a direct compression for core and erodible layer of phenylephrine on the top of the core. For the extended release tablet core, phenylephrine hydrochloride is first milled through a lab scale Cone mill using a 20 mesh screen. The hydroxypropyl cellulose klucel EXF, hydroxypropyl cellulose klucel GXF, carboxymethylcellulose sodium and one third portion of microcrystalline cellulose are passed through the same Cone mill. The milled materials are then mixed in an appropriate size of PK blender for 5 minutes. The rest of microcrystalline cellulose is added to the blend and mixed for additional 5 minutes. The magnesium stearate is screened through a 30-mesh screen, added to the blend and mixed for additional 3 minutes. The powder blend is then compressed into extended release cores using an extra deep cup 7/16" round tooling. The immediate release active coating layer as detailed immediately below is the first of two consecutive coated layers applied to the core of the tablet. Coating of the extended release cores can be performed using conventional coating equipment such as a lab scale conventional coating pan (O'Hara Labcoat MX) or conventional commercial scale equipment such as an Accela-Cota®. In the case of both immediate release and extended release coatings, appropriate excess coating should be prepared. Mixing vessels with a capacity of approximately double the final volume are typically used.

The active coating dispersion is prepared by first dissolving the Phenylephrine HCl in water while mixing under low shear. A polyvinyl alcohol based polymer (e.g., Opadry™ II 85F series (e.g., 18422 (White)) or polyvinyl alcohol-polyethylene glycol graft copolymer (e.g., Kollicoat IR) is then slowly added to the solution while mixing continues under low to moderate shear for at least one hour or until no visible clumps and/or agglomerated particles exist. Loratadine is then added to the dispersion. The Loratadine is typically allowed to dispersed and become incorporated into the dispersion under constant, moderate shear until no loratadine is observed on the surface of the dispersion. High shear using and Ultra Turrax mixer with a rotational speed of 5000-6200 rpm is then required to disperse the agglomerated Loratadine particles for 5 minutes. A recirculation high shear system could also be implored. A milky, white, uniform suspension should form with a solids content of 11.5-23%. This range of percentages has been evaluated and coated successfully on comparable tablets. Individual loratadine drug particles should be prevalent throughout the dispersion at this point. This dispersion should then be allowed to mix under low shear to de-gas for at least 1 hour or until the original solution volume is achieved, before spraying. The coating dispersion is uniform at this point and subsequently throughout the coating process. Coating continues until the desired weight gain is achieved based on gravimetric weight measurements. The blue finish coat dispersion is prepared by slowly adding the Opadry II 85F99001 (blue) to water while mixing continues under low to moderate shear for at least one hour or until no visible clumps and/or agglomerates exist. A milky, blue uniform suspension should form with a solids content of approximately 18%. Coating continues until the desired weight gain is achieved based on gravimetric weight measurements. Similar equipment determination, processing parameters and processing controls need to be established for the application of this coating dispersion as outlined above. The tablets are branded with Blue Opacode WB NS-78-10526 as per standard imprinting techniques so that a trace amount remains on the tablet surface.

In yet another embodiment, the composition comprises a bi-layer tablet with an immediate release layer and an extended release layer. In one preferred embodiment, the bi-layer tablet formulation is compressed together with an extended release layer comprising 22.5 mg phenylephrine hydrochloride and an immediate release layer comprising 7.5 mg phenylephrine hydrochloride and 5 mg loratadine (Table 10). In addition to 22.5 mg phenylephrine hydrochloride, the extended release layer comprises hydroxypropyl cellulose, carboxymethylcellulose sodium, microcrystalline cellulose and magnesium stearate. The immediate release layer comprises microcrystalline cellulose, colloidal silicon dioxide, crospovidone and magnesium stearate forming an immediate release layer with loratadine and Phenylephrine and or pharmaceutically acceptable phenylephrine salt. A colorant may add for improving the appearance or distinguish two layers.

TABLE 10

|  | Exemplary Formulation I/ Formulation II | | Exemplary | |
| --- | --- | --- | --- | --- |
|  | Weight Percent Ranges (w/w) of dosage form | mg/tablet | Weight Percent Ranges (w/w) of dosage form | mg/tablet |
| Extended release layer Components | | | | |
| Phenylephrine Hydrochloride | 3–4 | 22.5 | 3–4 | 22.5 |
| Hydroxypropyl Cellulose NF | 20–21 | 125 | 14.5–15.5 | 50 |
| Carboxymthylcellulose Sodium NF | 29–30 | 175 | 1–2 | 90 |
| Microcrystalline Cellulose NF | 27–28 | 167.5 | 55–56 | 332.5 |
| Colloidal Silicon Dioxide NF | 0.8–0.9 | 5 | 0–0.9 | 0 |
| Magnesium Stearate NF | 0.8–0.9 | 5 | 0.8–0.9 | 5 |
| Total Extended Layer Weight | | 500.00 | | 500.00 |
| Immediate release erodible layer Components | | | | |
| Loratadine, micronized | 0.8–0.9 | 5 | 0.8–0.9 | 5 |
| Phenylephrine Hydrochloride | 1–2 | 7.5 | 1–2 | 7.5 |
| Microcrystalline Cellulose NF | 0.5–1.5 | 81.4 | 0.5–1.5 | 81.4 |
| Colloidal Silicon Dioxide USP | 0.08–0.09 | 0.5 | 0.08–0.09 | 0.5 |
| Crospovidone NF | 0.8–0.9 | 5 | 0.8–0.9 | 5 |
| Magnesium Stearate NF | 0.08–0.09 | 0.5 | 0.08–0.09 | 0.5 |
| F D&C Blue No. 1 (optional) | 0.01–0.02 | 0.1 | 0.01–0.02 | 0.1 |
| Total Immediate Layer Weight | | 100 | | 100 |
| Total Tablet Weight | | 600 | | 600 |

In one particularly preferred embodiment, the components and amounts of the bi-layer composition are those detailed in Table 10 as Exemplary Formulation II.

The preferred manufacturing process is a direct compression tableting process using a bi-layer rotary tablet press. The preferred composition is a bi-layer tablet with two district tablets layer; the extended release layer and an immediate release layer. For the extended release tablet layer, phenylephrine hydrochloride is first milled through a lab scale Cone mill using a 20 mesh screen. The Hydroxypropyl Cellulose Klucel EXF, Hydroxypropyl Cellulose Klucel GXF, carboxymethylcellulose sodium and one third portion of microcrystalline cellulose are passed through the same Cone mill. The milled materials are than mixed in an appropriate size of PK blender for 5 minutes. The rest of microcrystalline cellulose is added to the blend and mixed for additional 5 minutes. The magnesium stearate is hand screened through a 30-mesh screen, added to the blend and mixed for additional 3 minutes and discharged into a container labeled with an appropriate label.

For the immediate release tablet layer, phenylephrine hydrochloride and loratadine are first milled through a lab scale Cone mill using a 20 mesh screen. The Blue No. 1 Lake, colloidal silicon dioxide, Crospovidone and one third portion of microcrystalline cellulose are passed through the same Cone mill. The milled materials are than mixed in an appropriate size of PK blender for 5 minutes. The rest of microcrystalline cellulose is added to the blend and mixed for additional 5 minutes. The magnesium stearate is hand screened through a 30-mesh screen, added to the blend and mixed for additional 3 minutes. The both powder blend, extended release and immediate release blends, are then compressed into bi-layer tablets with a hi-layer rotary tablet press using deep cup 7/16" round tooling.

General Process for Manufacturing the Formulations

Another aspect of the invention are the processes of manufacturing the formulations described above. The solid formulations are prepared using methods generally known in the at to prepare multiple-layered dosage forms. The formulations are in the form of tablets, capsules, gel-caps, or liqui-caps, among others. Stability and degradation analyses can be performed according to the International Conference on Harmonization (ICH) standards as described in "Impurities in New Drug Products" guidelines to simulate two or more years of shelf life. For example, stability testing can be performed at 40 degrees Celsius/75% relative humidity for a 3-month period. Standard pharmaceutical storage conditions are known in the art. Compositions according to the invention can be assayed to meet all ICH guidelines for active pharmaceutical assay with degradant levels which are below reporting limits, preferably below identification limits, and most preferably below qualification limits.

Methods of Treatments and Administration

Other aspects of the invention are methods of treating symptoms of cold, influenza, or allergies in subject in need thereof, comprising administering the pharmaceutical compositions described herein. In certain embodiments, the methods comprise administering the pharmaceutical composition every 8, 12, 16, or 24 hours.

Another aspect of the invention is a method of delivering at least a portion of phenylephrine or a pharmaceutically acceptable salt thereof to the colon of a subject comprising administering a formulation or composition of the invention to said subject. Compositions useful for the methods are the oral formulations or pharmaceutical compositions of the invention as described above. In certain embodiments, such method is a method wherein unconjugated phenylephrine is present in the plasma of the subject at least at about 5 hours after administration, and more preferably, between about 6 and about 12 hours after administration. In certain embodiments, such method is a method wherein the maximal concentration of unconjugated phenylephrine in the plasma of the subject is reached between about 5 and about 24 hours after administration, and more preferably, between about 6 and about 12 hours after administration. The method may be carried out for any subject currently considered suitable for administration of phenylephrine and any additional pharmaceutical agent.

In another aspect of the invention, the methods of the invention are methods for maintaining sustained bioavailability of phenylephrine in an unconjugated, therapeutically active form comprising administering by oral administration a pharmaceutical composition described herein, wherein at least a portion of phenylephrine is absorbed via the colon. In certain embodiments, unconjugated phenylephrine is bioavailable in the plasma for more than 4, 6, 8, 12, 16, or 24 hours after the administration. By bioavailable, it is meant that the active form of phenylephrine is quantifiable in the plasma of the subject, and preferably at more than 0.1 ng/mL, and even at 0.2, 0.3, 0.4, 0.5, 1.0, or 2.5 ng/mL. It is also an aspect of this invention that the plasma concentration of the unconjugated phenylephrine increases after more than about half an hour from the time of administration of the composition of the invention, and the maximum plasma concentration of the unconjugated phenylephrine is reached 1, 2, 4, 6, 8 or 12 hours after administration of the pharmaceutical composition.

Further an aspect of the invention is a method of administering phenylephrine by oral administration wherein a larger proportion of the unconjugated form of phenylephrine is preserved compared to a conventional administration of an immediate release oral formulation, resulting in an improved bioavailability and increased efficacy of the administered phenylephrine. In certain embodiments, the methods comprise administering a pharmaceutical composition of the invention with no immediate release component of phenylephrine, wherein the maximal plasma concentration of the unconjugated phenylephrine represents at least about 1% of the maximal plasma concentration of the total phenylephrine. In certain embodiments, the percentage is at least 2, 3, 4, 5, 6, or 7%. In comparison, the maximal plasma concentration of the unconjugated phenylephrine represents less than 0.7% of the maximal plasma concentration of the total phenylephrine when administered as an immediate release formulation by oral administration. It is understood that even when administering a pharmaceutical composition of the invention further comprising an immediate release portion of phenylephrine, the percentage of the active phenylephrine in the plasma is additive, and therefore always larger than if the total amount of phenylephrine was in immediate release inn administered orally.

In another aspect, the methods of the invention result in a higher relative $AUC_{0-4}$ and $AUC_{0-\infty}$ of unconjugated phenylephrine compared to the total phenylephrine in the plasma of a subject administered phenylephrine. $AUC_{0-24}$ is a parameter showing the cumulative plasma concentration for 24 hours after dosing, defined as the area under the concentration-time curve from dosing or activation to 24 hours after dosing; $AUC_{0-\infty}$ is parameter showing the total cumulative plasma concentration over time, defined as the calculated area under the concentration-time curve from dosing or activation to infinity. In certain embodiments, the methods of the invention comprise administering a pharmaceutical composition of the invention to a subject, wherein the $AUC_{0-24}$ value for the unconjugated phenylephrine in the plasma of the subject is at least 1% of the $AUC_{0-24}$ value for the total phenylephrine in the plasma of the subject. In a preferred embodiment, the relative $AUC_{0-24}$ value for the unconjugated phenylephrine is at least 2, 3, 4, 5, 6, or 7% of the $AUC_{0-24}$ value for the total phenylephrine.

Another aspect of the invention is a method of administering phenylephrine to a subject, comprising orally administering a pharmaceutical composition for delivery to the colon comprising phenylephrine to the subject, wherein phenylephrine is released in the colon, thereby achieving a minimal pre-systemic modification of phenylephrine. By minimal it is meant to be significantly less than such modification seen with oral administration of an immediate release currently available conventional phenylephrine or pharmaceutically acceptable salt thereof comprising composition.

It should also be understood that a specific dosage and treatment regimen for any particular patient will depend upon a variety of factors. Such factors include the age, body weight, general health, sex, diet, drug combination, and the judgement of the treating physician and the severity of the particular condition being treated. For any additional therapeutic agent, the dosage will also depend upon which particular compound(s) is/are in the composition, the activity of the specific compound(s) employed, bioavailability of the compound(s), and rate of excretion and degradability. The actual dosage suitable for a subject can easily be determined as a routine practice by one skilled in the art, for example a physician or a pharmacist.

The contents of any patents, patent applications, patent publications, or scientific articles referenced anywhere in this application are herein incorporated by reference in their entirety.

The following experimental examples are intended to be illustrative of the disclosed invention. The examples are non-limiting, and the skilled artisan will recognize that other embodiments are within the scope of the disclosed invention.

EXPERIMENTS EXAMPLES

Example 1

Bioavailability of Phenylephrine

The following study was conducted to examine the phenylephrine absorption behavior in GI tract. Healthy male and non-pregnant, non-breast-feeding healthy female subjects were dosed with 10 mg phenylephrine hydrochloride delivered to the colon via the Enterion™ capsules (regimen A—nine subjects), with 10 mg Sudafed PE™ (regimen B—eight subjects), or 30 mg phenylephrine hydrochloride delivered to the colon via the Enterion™ capsules (regimen C—eight subjects), all administered orally, after overnight fasting. Enterion™ capsules (Pharmaceutical Profiles Ltd, UK) allow for deployment of drug delivery at a desired location within the GI tract. To determine the capsules had reached a desired location, preparations of regimens A and C were administered orally with 210 mL water followed by a radiolabeled drink containing 4 MBq 99m-Tc-diethylenetriaminepetaacetic acid (DTPA) in 30 mL water so that the location of the ingested materials could be visualized by scintigraphic imaging. Enterion™ capsules were successfully activated and phenylephrine was released in 8 of 9 subjects in regimen A and 6 of 8 subjects in regimen C. Plasma concentrations of phenylephrine, both in an unconjugated active form, or a conjugated inactivated form, were determined by withdrawing venous blood samples at 0, 5, 15, 30, 45 minutes, and 1, 1.5, 2, 2.5, 3, 4, 6, 8, 12, 14, 16 and 24 hours post capsule activation or dose. The blood samples were collected into a tube containing lithium heparin, centrifuged within 30 minutes at 1500 g for 15 minutes at 4 degrees Celsius. The plasma was analyzed for phenylephrine in its conjugated and unconjugated forms. The amount of conjugated phenylephrine was calculated by subtracting the amount of unconjugated phenylephrine assayed from the amount of total phenylephrine assayed.

Figure 6A:
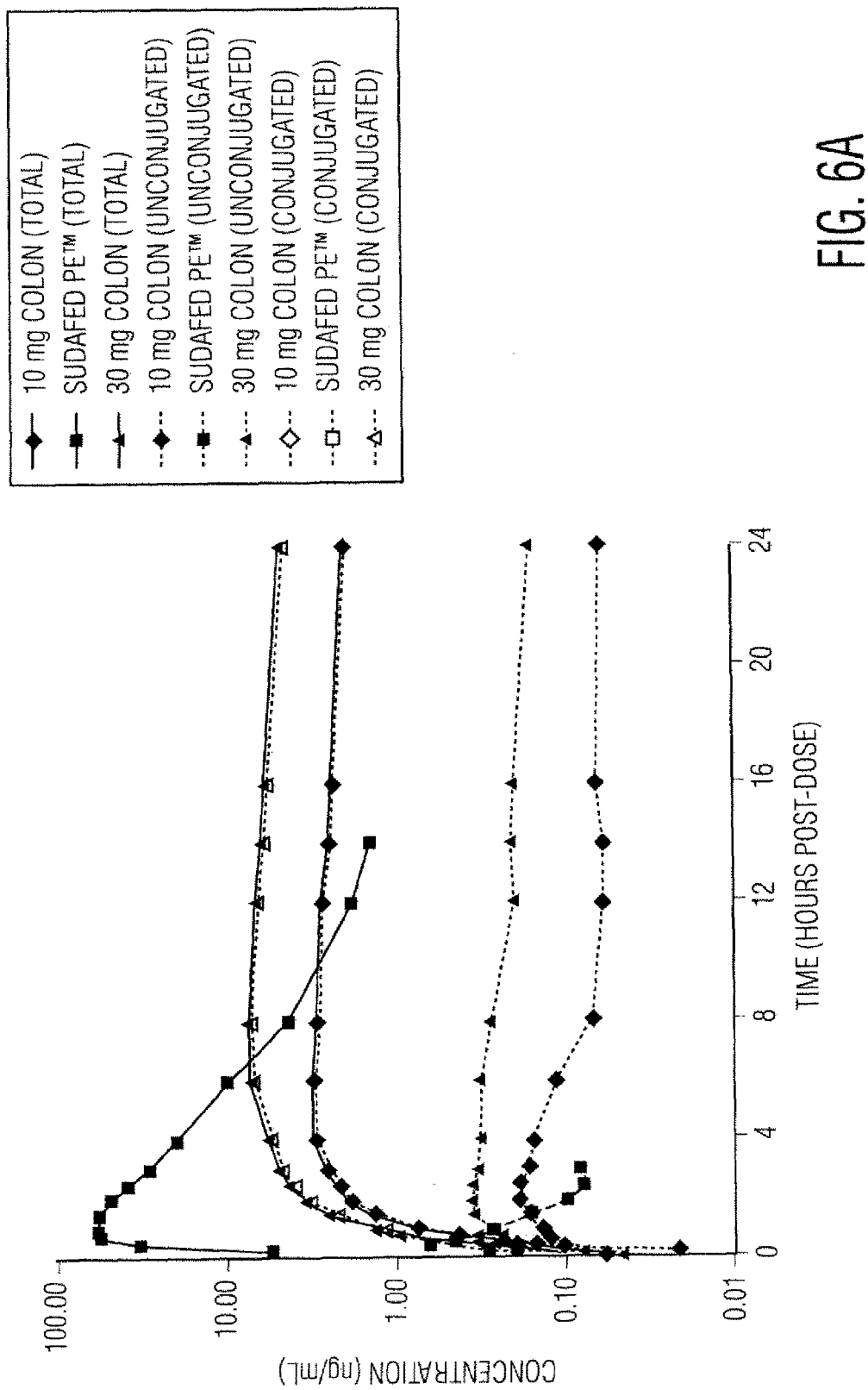
FIG. 6A shows a semi-logarithmic plot.
Figure 6B:
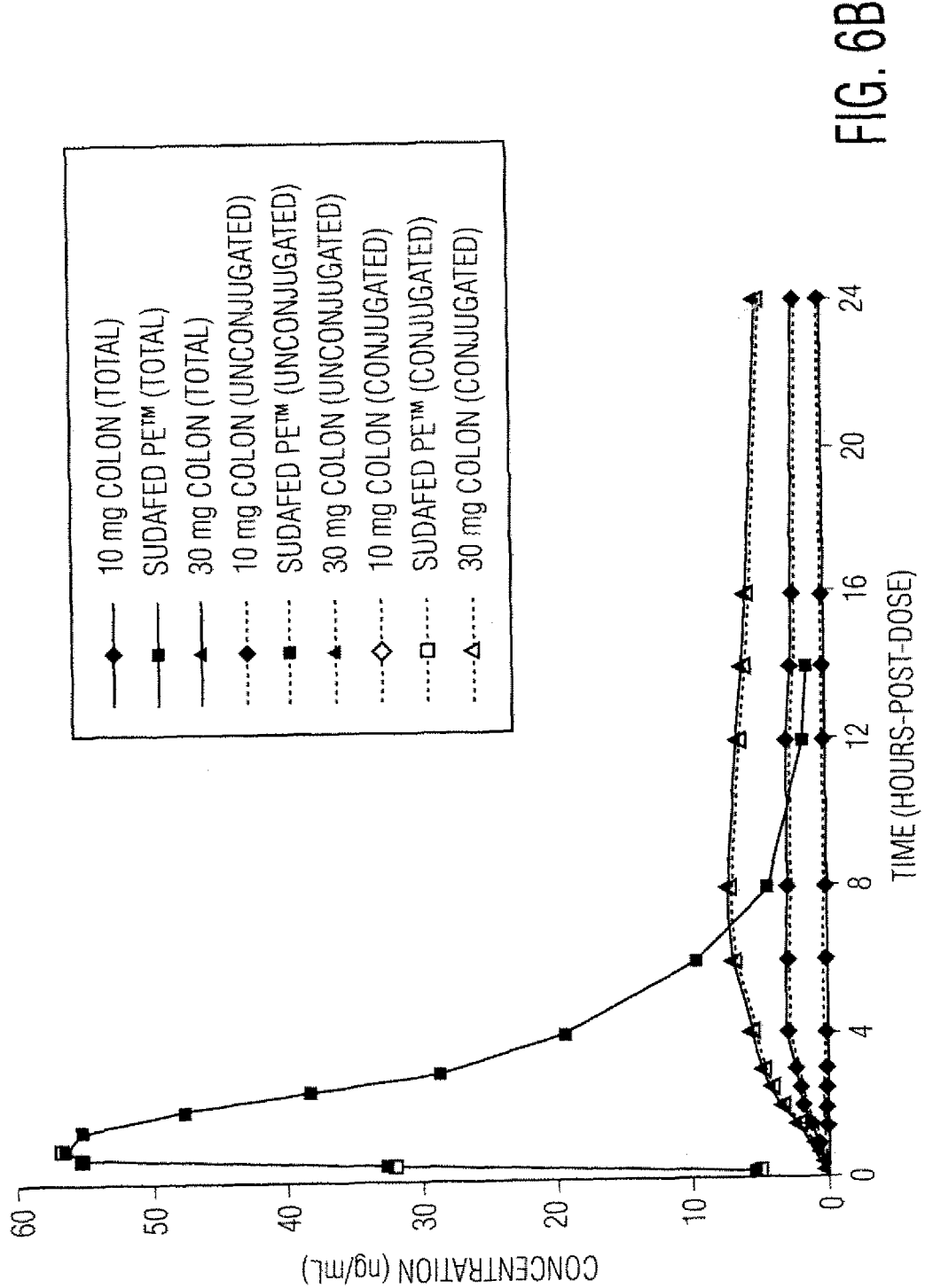
FIG. 6B shows a linear plot. In addition.
Figure 6C:
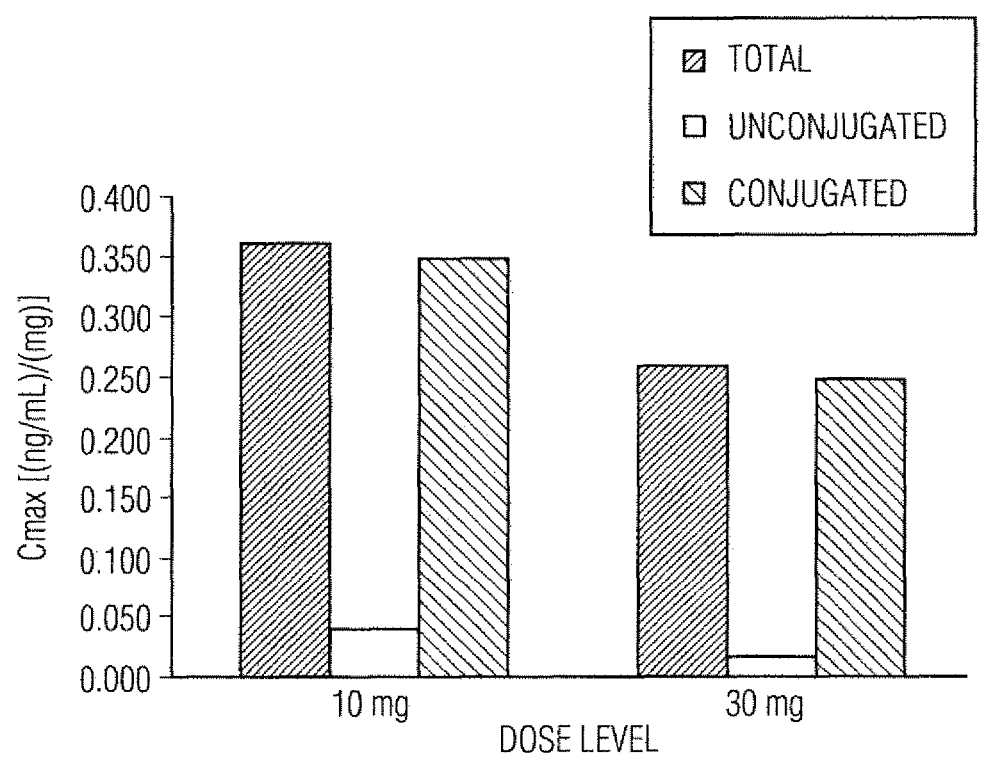
FIG. 6C shows a chart of the mean Cmax of total, as well as conjugated and unconjugated phenylephrine, adjusted to a dose level of 1 mg, following delivery of 10 mg and 30 mg phenylephrine to the colon.

The mean plasma concentration of total as well as unconjugated phenylephrine detailed in Table 11 below are illustrated in FIG. 6. In particular, FIG. 6A shows a semi-logarithmic plot, and FIG. 6B shows a linear plot. Although present in both FIGS. 6A and 6B, the plots for conjugated phenylephrine generally overlay those for total phenylephrine and are thus difficult to distinguish. The similarity between total and conjugated phenylephrine is evident in FIG. 6C which charts the mean Cmax of total, unconjugated and conjugated phenylephrine adjusted to a dose level of 1 mg, following delivery of 10 mg and 30 mg phenylephrine to the colon. As illustrated in FIG. 6A, the plot for unconjugated phenylephrine from the Sudafed PE™ peaks rapidly and then declines rapidly to a level below 0.1 ng/ml within the first 4 hours post-dose. In contrast, the plots for both 10 mg and 30 mg doses of unconjugated phenylephrine delivered to the colon peak and decline more gradually and are fairly constant for an extended period of time.

The data were analyzed using a standard pharmacokinetic analysis method for the following parameters; $C_{max}$, the maximal plasma concentration observed; $T_{max}$, the time to reach $C_{max}$; $T_{lag}$, the time when the drug was first quantifiable in the plasma; $AUC_{0-24}$, the area under the concentration-time curve from dosing or activation to 24 hours after; $AUC_{0-\infty}$, the area under the concentration-time curve from dosing or activation to infinity; $t_{1/2}$, terminal elimination half life. The relative bioavailability, shown as $F_{rel}$ last in the table, indicates the bioavailability of phenylephrine administered to the colon relative to that administered as an immediate release oral formulation. The results are shown in Tables 11, 12, and 13. In addition, the plasma concentration profiles of total as well as unconjugated phenylephrine are presented graphically in FIG. 6.

The plasma concentration of immediate release phenylephrine formulation peaked quickly after oral administration in about 1.5 hours, and rapidly dropped to half maximal concentration by 2.5 hours (see Tables 11, 12, and 13). In comparison, phenylephrine delivered and absorbed through the colon reached its maximum concentration in about 6 hours (10 mg) or 8 hours (30 mg), slowly decreasing in concentration to reach half maximal concentration by about 12 hours (10 mg).

Further, the active unconjugated form accounted only for a very small portion of the plasma concentration of phenyleph-

TABLE 11

| Mean plasma concentration | Time (hours post-dose) | | | | | | | | |
|---|---|---|---|---|---|---|---|---|---|
| | 0 | 0.083 | 0.25 | 0.5 | 0.75 | 1 | 1.5 | 2 | 2.5 |
| 10 mg Colon (Total) | | | 0.205 | 0.260 | 0.333 | 0.746 | 1.36 | 1.96 | 2.13 |
| Sudafed PE ™ (Total) | | 5.43 | 32.7 | 55.4 | 56.8 | 55.3 | 47.8 | 38.3 | |
| 30 mg Colon (Total) | | | 0.335 | 0.945 | 1.28 | 2.44 | 3.47 | 4.15 | |
| 10 mg Colon (Unconjugated) | | 0.0586 | 0.304 | 0.145 | 0.125 | 0.135 | 0.160 | 0.187 | 0.182 |
| Sudafed PE ™ (Unconjugated) | | | 0.278 | 0.641 | 0.431 | 0.271 | 0.156 | 0.0945 | 0.0779 |
| 30 mg Colon (Unconjugated) | | 0.0458 | 0.0784 | 0.229 | 0.242 | 0.253 | 0.348 | 0.354 | 0.352 |
| 10 mg Colon (Conjugated) | | | 0.0213 | 0.186 | 0.301 | 0.673 | 1.22 | 1.80 | 1.97 |
| Sudafed PE ™ (Conjugated) | | 5.17 | 32.1 | 55.0 | 56.5 | 55.2 | 47.7 | 38.3 | |
| 30 mg Colon (Conjugated) | | | 0.239 | 0.726 | 1.07 | 2.11 | 3.12 | 3.79 | |

| Mean plasma concentration | Time (hours post-dose) | | | | | | | |
|---|---|---|---|---|---|---|---|---|
| | 3 | 4 | 6 | 8 | 12 | 14 | 16 | 24 |
| 10 mg Colon (Total) | 2.53 | 3.06 | 3.07 | 2.86 | 2.68 | 2.42 | 2.34 | 1.94 |
| Sudafed PE ™ (Total) | 28.8 | 19.5 | 9.61 | 4.26 | 1.77 | 1.39 | | |
| 30 mg Colon (Total) | 4.88 | 5.53 | 6.93 | 7.33 | 6.50 | 6.01 | 5.71 | 4.59 |
| 10 mg Colon (Unconjugated) | 0.165 | 0.150 | 0.111 | 0.068 | 0.058 | 0.059 | 0.064 | 0.059 |
| Sudafed PE ™ (Unconjugated) | 0.0811 | | | | | | | |
| 30 mg Colon (Unconjugated) | 0.324 | 0.309 | 0.311 | 0.269 | 0.195 | 0.204 | 0.196 | 0.157 |
| 10 mg Colon (Conjugated) | 2.36 | 2.91 | 2.96 | 2.79 | 2.62 | 2.38 | 2.30 | 1.91 |
| Sudafed PE ™ (Conjugated) | 28.8 | 19.5 | 9.61 | 4.26 | 1.77 | 1.39 | | |
| 30 mg Colon (Conjugated) | 4.56 | 5.22 | 6.61 | 7.06 | 6.30 | 5.81 | 5.51 | 4.43 | rine, which rapidly reached its maximal plasma concentration and was eliminated when administration was as an immediate release form. The proportion of the active, unconjugated phenylephrine compared to the total phenylephrine that was available in the plasma over time can be determined by dividing the $AUC_{0-\infty}$ of the unconjugated phenylephrine by the $AUC_{0-\infty}$ of the total phenylephrine. When 10 mg phenylephrine was administered in immediate release form, the active unconjugated form of phenylephrine accounted at most only for approximately 0.5% of the total phenylephrine concentration over time detected in the plasma. In comparison, when 10 mg phenylephrine was administered by a release in the colon, the active unconjugated form of phenylephrine accounted for approximately 2.2% of the total phenylephrine concentration over time detected in the plasma. Approximately 5% of the total phenylephrine was available in the active form when 30 mg phenylephrine was administered by a release in the colon.

post dose, of unconjugated phenylephrine was 0.561±0.165 ng·h/mL and the terminal half-life ranged from 0.323 to 3.52 hours. These data for unconjugated phenylephrine are in close agreement with published information on the pharmacokinetics of phenylephrine.

Delivery of 10 mg phenylephrine hydrochloride to the colon resulted in a reduction in $C_{max}$ and a prolonged $T_{max}$ for unconjugated phenylephrine compared with the immediate release formulation. However, the $AUC_{0-24}$ values for unconjugated phenylephrine were higher than those values for the Sudafed PE™. $T_{max}$ was variable and ranged from 0.25 to 3 hours. The mean $C_{max}$ value was 0.400±0.454 ng/mL and the mean $AUC_{0-24}$ value was 1.58±0.915 ng·h/mL. The terminal half-life ranged from 2.91 to 13.5 hours which is longer than the values reported for the immediate release tablet. The data

TABLE 12

Mean ± SD values of pharmacokinetic parameters for total Phenylephrine

| Parameter | 10 mg PE-colon (Regimen A) n = 8 | 10 mg Sudafed PE ™ (Regimen B) n = 9 | 30 mg PE-colon (Regimen C) n = 6 |
|---|---|---|---|
| $C_{max}$ (ng/mL) | 3.61 ± 1.60 | 63.6 ± 27.5 | 7.75 ± 2.60 |
| $T_{max}$ (hours) | 6.00 (3.00–16.0)$_a$ | 1.50 (0.750–2.00)$_a$ | 8.00 (2.50–12.0)$_a$ |
| $T_{lag}$ (hours) | 0.875 (0.0800–2.50)$_a$ | 0.08 (0.08–0.25)$_a$ | 0.75 (0.00–1.50)$_a$ |
| $AUC_{0-24}$ (ng/h/mL) | 46.7 ± 28.5 | 198 ± 65.4 | 122 ± 52.0 |
| $AUC_{0-\infty}$ (ng.h/mL) | 81.7 ± 51.5 (n = 5) | 201 ± 69.7 (n = 8) | 179 (n = 2) |
| $t^{1/2}$ (hours) | 9.40 ± 4.94 (n = 5) | 1.99 ± 0.732 (n = 8) | 7.57 (n = 2) |
| Frel last % | 22.3 ± 8.46 | | 20.2 ± 5.47 |

$_a$Median (range)

TABLE 13

Mean ± SD values of pharmacokinetic parameters for unconjugated Phenylephrine

| Parameter | 10 mg PE-colon (Regimen A) n = 8 | 10 mg Sudafed PE ™ (Regimen B) n = 9 | 30 mg PE-colon (Regimen C) n = 6 |
|---|---|---|---|
| $C_{max}$ (ng/mL) | 0.400 ± 0.454 | 0.704 ± 0.369 | 0.468 ± 0.174 |
| $T_{max}$ (hours) | 1.50 (0.250–3.00)$_a$ | 0.500 (0.250–0.750)$_a$ | 2.25 (0.750–6.03)$_a$ |
| $T_{lag}$ (hours) | 0.0800 (0–0.750)$_a$ | 0.0800 (0.0800–0.250)$_a$ | 0 (0–0.750)$_a$ |
| $AUC_{0-24}$ (ng.h/mL) | 2.87 (n = 2) | 0.640 ± 0.268 (n = 5) | 8.94 ± 5.16 (n = 3) |
| $t^{1/2}$ (hours) | 8.19 (n = 2) | 1.11 ± 1.36 (n = 5) | 10.8 ± 7.99 (n = 3) |
| Frel last % | 332 ± 232 | | 333 ± 140 |

$^a$Median (range)

TABLE 14

Mean ± SD values of pharmacokinetic parameters for conjugated Phenylephrine

| Parameter | 10 mg PE-colon (Regimen A) n = 8 | 10 mg Sudafed PE ™ (Regimen B) n = 9 | 30 mg PE-colon (Regimen C) n = 6 |
|---|---|---|---|
| $C_{max}$ (ng/mL) | 3.47 ± 1.58 | 63.3 ± 27.4 | 7.43 ± 2.62 |
| $T_{max}$ (hours) | 6.00 (3.00–16.0)$_a$ | 1.50 (0.750–2.000)$_a$ | 8.00 (2.50–12.00)$_a$ |
| $T_{lag}$ (hours) | 0.875 (0.0800–22.50)$_a$ | 0.0800 (0.0800–0.250)$_a$ | 0.750 (0–1.50)$_a$ |
| $AUC_{0-24}$ (ng.h/mL) | 45.2 ± 28.3 | 198 ± 65.3 | 114 ± 55.4 |
| $AUC_{0-\infty}$ (ng.h/mL) | 80.9 ± 51.9 (n = 5) | 200 ± 69.7 (n = 8) | 174 (n = 2) |
| $t^{1/2}$ (hours) | 9.68 ± 4.99 (n = 5) | 2.02 ± 0.747 (n = 8) | 7.57 (n = 2) |
| Frel last % | 21.6 ± 8.38 | | 18.5 ± 5.98 |

$_a$Median (range)

Administration of the immediate release tablet, Sudafed PE™, resulted in rapid absorption of unconjugated phenylephrine. The $T_{max}$ ranged from 0.25 to 0.75 hours post-dose and the mean $C_{max}$ value was 0.704±0.369 ng/mL. The $AUC_{0-24}$ value, showing the total amount of drug residing in the plasma over time between the dosing time and 24 hours suggest that absorption in the colon was rate-limiting on the elimination and that the terminal phase therefore indicates continued absorption.

As with the delivery of 10 mg phenylephrine hydrochloride to the colon, the delivery of 30 mg phenylephrine hydrochloride resulted in prolonged absorption with a prolonged $T_{max}$ and a reduced $C_{max}$ for unconjugated phenylephrine. $T_{max}$ ranged from 0.75 to 6.03 hours and the mean $C_{max}$ value was 0.468±0.174 ng/mL. The mean $AUC_{0-24}$ value was 5.17±1.56 ng·h/mL and the mean relative bioavailability was 333±140% (range 213 to 544%) as compared to the bioavailability measured for an oral administration of phenylephrine in its immediate release form. The terminal half-life ranged from 2.98 to 18.9 hours.

The results surprisingly show that the colonic absorption of phenylephrine demonstrates a more desirable sustained plasma concentration as compared to the immediate release oral administration of phenylephrine, and that a higher proportion of phenylephrine remains in the unconjugated active form. The colonic absorption, however, lacks the initial burst that the immediate release oral administration affords.

Example 2

Exemplary Formulations A-G were Made and the Dissolution Profiles Determined

The dissolution profiles of Exemplary Formulations A-G (detailed in Table 2) were examined over a 14 hour time period using a USP I dissolution apparatus set at 75 rpm. The dissolution study was conducted at 37° C.±0.5° C. with 900 ml water buffered with 0.5 mM phosphate buffer at pH 7.4. At each time interval, a sample of the solution was analyzed by HPLC at 215 nm to determine the percent phenylephrine dissolved. The dissolution results, which are an average of 3 runs, are shown in Table 15. Likewise, the dissolution profile is presented in FIG. 3.

TABLE 15

| Time | % Phenylephrine Dissolved for Exemplary Formulations A–G | | | | | | |
|---|---|---|---|---|---|---|---|
| (hr) | A | B | C | D | E | F | G |
| 0 | 0 | 0 | 0 | 0 | 0 | 0 | 0 |
| 0.3 | 3.9 | 5.3 | 7.0 | 5.4 | 7.0 | 7.1 | 5.2 |
| 0.5 | 7.6 | 8.3 | 9.7 | 10.3 | 12.1 | 10.6 | 9.5 |
| 0.75 | 10.7 | 10.2 | 11.4 | 15.2 | 20.3 | 13.2 | 12.7 |
| 1 | 13.4 | 12.2 | 12.9 | 20.6 | 20.5 | 15.8 | 15.2 |
| 2 | 27.4 | 19.5 | 18.5 | 44.2 | 41.1 | 28.4 | 28.8 |
| 3 | 44.0 | 27.8 | 24.7 | 67.2 | 60.6 | 44.0 | 46.9 |
| 4 | 60.8 | 36.5 | 31.4 | 89.1 | 77.6 | 58.5 | 63.8 |
| 5 | 77.6 | 45.1 | 38.3 | 101.7 | 92.9 | 73.5 | 80.8 |
| 6 | 89.3 | 54.7 | 45.3 | 107.7 | 102.3 | 87.3 | 94.8 |
| 8 | 102.9 | 74.8 | 60.0 | 109.2 | 104.7 | 98.2 | 106.0 |
| 10 | 105.7 | 92.0 | 75.8 | 110.0 | 106.9 | 100.6 | 107.7 |
| 12 | 106.4 | 100.3 | 90.3 | 110.5 | 108.2 | 102.4 | 108.6 |
| 14 | 106.8 | 101.7 | 101.1 | 110.9 | 109.5 | 103.6 | 109.3 |

Example 3

Figure 4:
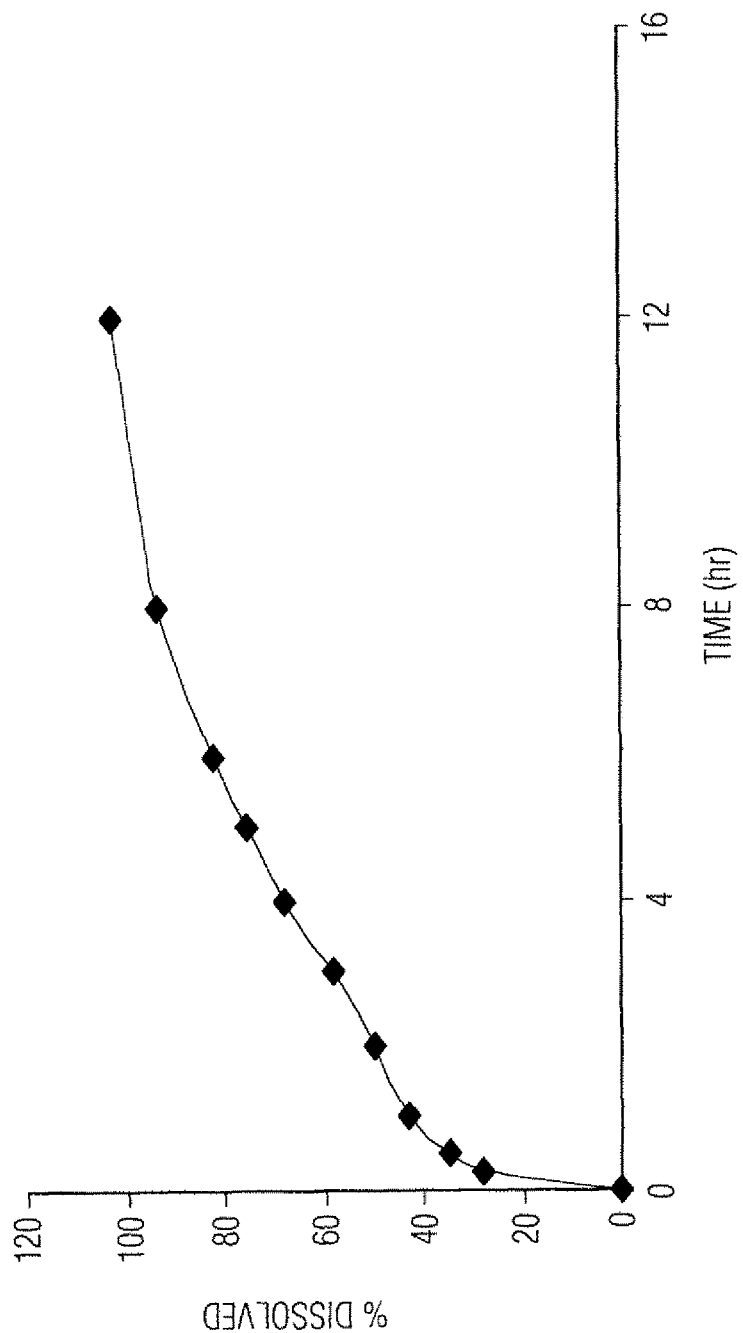
FIG. 4 shows the dissolution profile of an exemplary preferred formulation comprising an extended release tablet core wherein the components comprise 22.5 mg phenylephrine hydrochloride and an immediate release active coating encapsulating the core wherein the components comprise 7.5 mg phenylephrine hydrochloride and 5 mg loratadine.

The Exemplary Formulation Detailed in Table 9 was Made and the Dissolution Profiles Determined The release profile of phenylephrine from a tablet according to the example detailed in Table 9 was studied over a 12 hours time period using USP II dissolution apparatus starting at 50 rpm. The dissolution study was conducted with 750 ml of simulated gastric fluid TS USP (no enzymes) for first one hour. After an hour the pH of the medium was raised to pH 6.8 by adding 250 mL 2.0M Sodium Tri Phosphate solution and the dissolution study was continued for additional 11 hours. At each time interval, a sample of the solution was analyzed to determine the percent phenylephrine dissolved. FIG. 4 presents the data graphically.

Example 4

Figure 5:
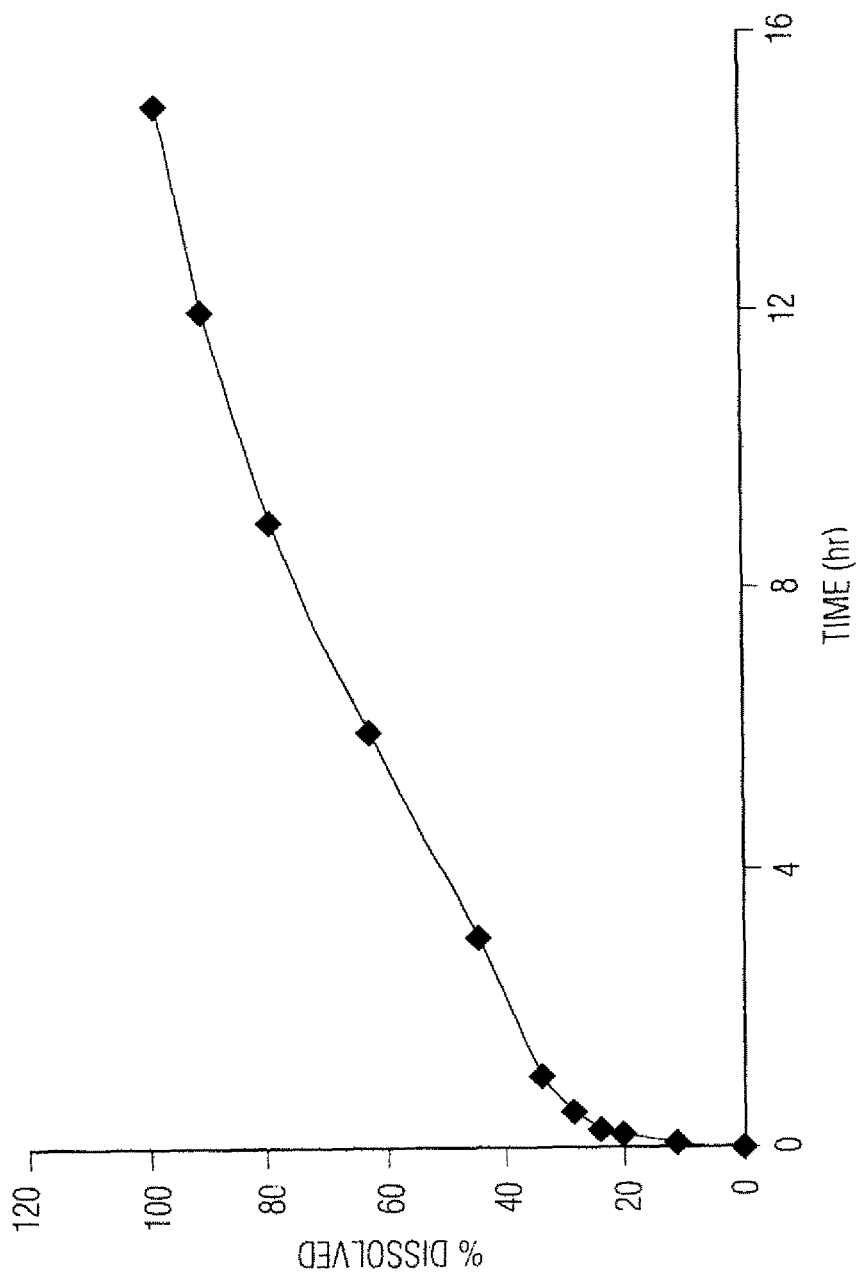
FIG. 5 shows the dissolution profile of a bi-layer tablet comprising a layer of phenylephrine formulated for sustained release and a layer of phenylephrine and loratadine formulated for immediate release.

The Exemplary Formulation Detailed in Table 10 was Made and the Dissolution Profiles Determined The release profile of phenylephrine from a hi-layer tablet according to Exemplary Formulation I detailed in Table 10 was studied over a 12 hours time period. The release profile of phenylephrine from a tablet according to example was studied over a 12 hours time period using USP II dissolution apparatus starting at 50 rpm. The dissolution study was conducted with 750 mL of simulated gastric fluid TS USP (no enzymes) for first one hour. After an hour the pH of the medium was raised to pH 6.8 by adding 250 mL 2.0M Sodium Tri Phosphate solution and the dissolution study was continued for additional 11 hours. At each time interval, a sample of the solution was analyzed to determine the percent phenylephrine dissolved. FIG. 5 illustrates the dissolution profile based on an average of 6 runs.

Example 5

Pharmacokinetic Model of Phenylephrine Absorption in the GI Tract

To aid understanding of how the dose, the release rate and the absorptive region of the GI tract affect the plasma concentration levels, a pharmacokinetic model was developed by incorporating the differential absorption along the GI tract and the drug release kinetics as an input function, for the purpose of predicting the unconjugated phenylephrine plasma concentrations. Preferred ranges for delivery of a portion of phenylephrine as immediate release (IR) to the upper GI tract, sustained release (SR) to the upper GI tract, and/or colonic delivery for both 30 mg and 60 mg phenylephrine (PE) dose scenarios are summarized in Table 16.

TABLE 16

| | Ranges for 30 mg PE dose scenario | Ranges for 60 mg PE dose scenario |
|---|---|---|
| Portion of dose delivered as immediate release to upper GI (mg)-IR | 0–15 | 0–30 |
| Portion of dose delivered as sustained release to upper GI (mg)-SR | 0–25 | 0–50 |
| Portion of dose delivered to colon (mg)-Colonic | 0–30 | 0–60 |

The results of simulations for a 10 mg immediate release dose of phenylephrine as well as 30 mg phenylephrine dose scenarios covering the ranges detailed in Table 16 are presented in Table 17 as well as graphically in FIG. 7. Based on the results of these simulations, the preferred embodiment for a 30 mg phenylephrine dose provides the following delivery profile, about 7.5 mg of phenylephrine delivered in an immediate release form to the upper GI tract and the remainder of phenylephrine delivered in a sustained release form to the upper GI tract and/or colon (e.g., about 17.5 mg of phenylephrine delivered in a sustained release form to the upper GI tract, and about 5 mg of phenylephrine delivered to the colon).

TABLE 17

| 30 mg Phenylephrine Dose Scenarios | $C_{max}$ ng/mL | [a]$C_{12Hr}$ ng/mL | $AUC_{0-\infty}$ ng/mL * hr | Relative Bioavailability Compared to [b]3X Sudafed PE 10 mg Tablet ($AUC_{0-\infty}$ of Scenario/$AUC_{0-\infty}$ Ref.) |
|---|---|---|---|---|
| 10 mg IR only | 0.751 | 0.006 | 0.9976 | — |
| 15 mg IR + 15 mg SR | 1.316 | 0.038 | 4.3208 | 1.44 |
| 5 mg IR + 25 mg SR | 0.752 | 0.082 | 6.3788 | 2.13 |
| 10 mg IR + 10 mg SR + 10 mg Colonic | 0.781 | 0.128 | 6.0051 | 2.01 |
| 10 mg IR + 7.5 mg SR + 12.5 mg Colonic | 0.774 | 0.129 | 6.2558 | 2.09 |
| 4 mg IR + 13 mg SR + 13 mg Colonic | 0.420 | 0.148 | 6.5986 | 2.20 |
| 4 mg IR + 9.75 mg SR + 16.25 mg Colonic | 0.330 | 0.171 | 7.4090 | 2.48 |
| 15 mg SR + 15 mg Colonic | 0.486 | 0.164 | 7.1112 | 2.38 |
| 11.5 mg SR + 18.5 mg Colonic | 0.274 | 0.186 | 7.9095 | 2.64 |
| 30 mg Colonic | 0.280 | 0.237 | 9.3762 | 3.13 |

Figure 8:
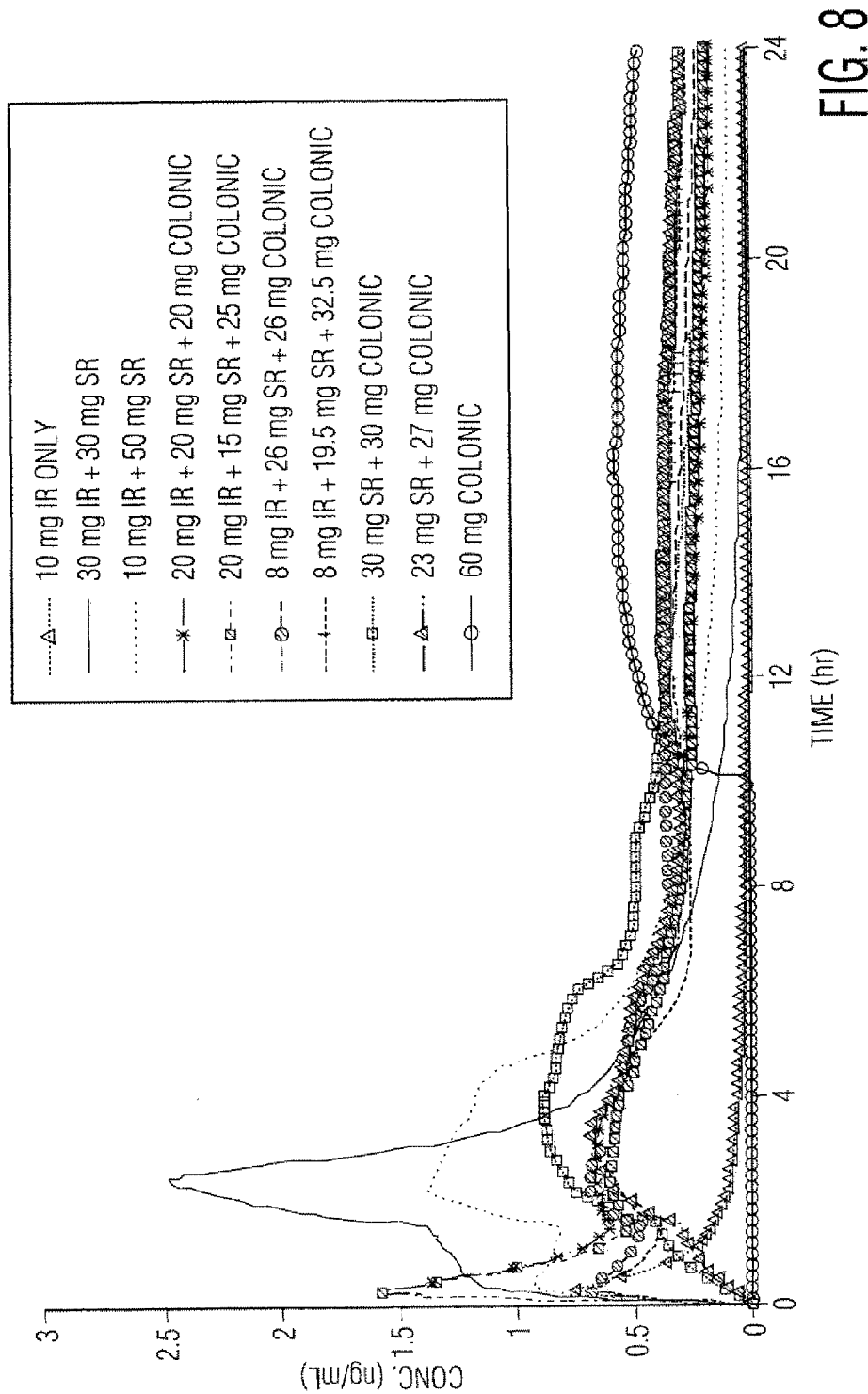
FIG. 8 shows simulated plasma concentration profiles for a 10 mg immediate release dose of phenylephrine as well as 60 mg phenylephrine dose scenarios (detailed in Table 18) covering the ranges detailed in Table 16.

[a]Phenlephrine plasma concentration 12 hours after dose administration
[b]Reference is Sudafed PE 10 mg tablet given every 4 hours for 12 hours The results of simulations for a 10 mg immediate release dose of phenylephrine as well as 60 mg phenylephrine dose scenarios covering the ranges detailed in Table 16 are presented in Table 18 as well as graphically in FIG. 8. Based on the results of these simulations, the preferred embodiment for a 60 mg phenylephrine dose provides the following delivery profile: about 10 mg of phenylephrine delivered in an immediate release form to the upper GI tract and the remainder of phenylephrine delivered in a sustained release form to the upper GI tract and/or colon (e.g., about 20 mg of phenylephrine delivered in a sustained release form to the upper GI tract, and about 30 mg of phenylephrine delivered to the colon).

TABLE 18

| 60 mg Phenylephrine Dose Scenarios | $C_{max}$ ng/mL | [a]$C_{24Hr}$ ng/mL | $AUC_{0-\infty}$ ng/mL * hr | Relative Bioavailability Compared to [b]6X Sudafed PE 10 mg Tablet ($AUC_{0-\infty}$ of Test/$AUC_{0-\infty}$ Ref.) |
|---|---|---|---|---|
| 10 mg IR only | 0.751 | 0.006 | 0.9976 | — |
| 30 mg IR + 30 mg SR | 2.476 | 0.012 | 8.7445 | 1.46 |
| 10 mg IR + 50 mg SR | 1.390 | 0.076 | 11.9906 | 1.85 |
| 20 mg IR + 20 mg SR + 20 mg Colonic | 1.562 | 0.150 | 11.9906 | 2.00 |
| 20 mg IR + 15 mg SR + 25 mg Colonic | 1.5472 | 0.168 | 12.2457 | 2.05 |
| 8 mg IR + 26 mg IR + 26 mg Colonic | 0.689 | 0.211 | 14.0798 | 2.35 |
| 8 mg IR + 19.5 mg SR + 32.5 mg Colonic | 0.660 | 0.252 | 14.6707 | 2.45 |
| 30 mg SR + 30 mg Colonic | 0.892 | 0.186 | 14.3403 | 2.40 |
| 23 mg SR + 37 mg Colonic | 0.683 | 0.276 | 15.7538 | 2.63 |
| 60 mg Colonic | 0.559 | 0.463 | 18.7524 | 3.13 |

[a]Phenylephrine plasma concentration 24 hours dose administration
[b]Reference is Sudafed PE 10 mg tablet given every 4 hours for 24 hours For embodiments described herein, the compositions comprising phenylephrine or a pharmaceutically acceptable salt thereof in the described core, layer(s) and coating are expected to exhibit plasma concentration profiles such as shown in FIG. 7 and FIG. 8. Therefore, given the specific teaching of this specification one skilled in the art can practice the invention, without undue experimentation, to achieve a desired dosage profile.

The invention claimed is:

1. A pharmaceutical composition comprising phenylephrine and having two portions, wherein a first portion comprises phenylephrine in an immediate release form, which releases phenylephrine in a human's upper gastrointestinal system, and a second portion comprises phenylephrine in a sustained release form, which releases at least a portion of phenylephrine in a human's colon, wherein the composition contains 30 mg of phenylephrine and provides a mean $C_{max}$ and at least one of a mean $AUC_{inf}$ and the mean $AUC_{0-12}$ for phenylephrine under fasted conditions based on a single-dose administration that are from 80% to 125% of the mean $C_{max}$ and at least one of the mean $AUC_{inf}$ and the mean $AUC_{0-12}$ for phenylephrine provided by an extended release tablet containing 30 mg of phenylephrine and having an extended release core consisting essentially of about 22.5 mg of phenylephrine hydrochloride, about 25 mg of hydroxypropyl cellulose 300-600 cPs at 10%, about 25 mg of hydroxylpropyl cellulose 150-300 cPs at 2%, about 90 mg of carboxymethylcellulose sodium, about 332.5 mg of microcrystalline cellulose, and about 5 mg of magnesium stearate, and an immediate release coating layer consisting essentially of about 7.5 mg phenylephrine hydrochloride and about 36 mg polyvinylalcohol-based polymer.

2. The composition according to claim 1, wherein phenylephrine is absorbed into the bloodstream such that the composition can be appropriately dosed once in a 12-hour period.

3. The composition according to claim 1, wherein the composition completely dissolves within 4-12 hours of ingestion.

4. The composition according to claim 1, wherein the phenylephrine dissolution profile of the composition comprises a zero-order release rate.

5. The composition according to claim 1, wherein the mean $C_{max}$ and at least one of a mean $AUC_{inf}$ and the mean $AUC_{0-12}$ for phenylephrine provided by the composition are from about 80% to 125% of the mean $C_{max}$ and at least one of the mean $AUC_{inf}$ and the mean $AUC_{0-12}$ for phenylephrine provided by the extended release tablet at a 90% confidence interval.

6. The composition according to claim 1, in which the extended release form comprises a polymer matrix.

7. The composition according to claim 1 or 6, in which the immediate release form comprises a coating.

8. A pharmaceutical composition comprising phenylephrine and having two portions, wherein a first portion comprises phenylephrine in an immediate release form, which releases phenylephrine in a human's upper gastrointestinal system, and a second portion comprises phenylephrine in a sustained release form, which releases at least a portion of phenylephrine in a human's colon, wherein the composition contains 30 mg of phenylephrine and provides a mean $C_{max}$ and a mean $AUC_{0-4}$ for phenylephrine under fasted conditions based on a single-dose administration that are from 80% to 125% of the mean $C_{max}$ and the mean $AUC_{0-4}$ for phenylephrine provided by an extended release tablet containing 30 mg of phenylephrine and having an extended release core consisting essentially of about 22.5 mg of phenylephrine hydrochloride, about 25 mg of hydroxypropyl cellulose 300-600 cPs at 10%, about 25 mg of hydroxypropyl cellulose 150-300 cPs at 2%, about 90 mg of carboxymethyl cellulose sodium, about 332.5 mg of microcrystalline cellulose, and about 5 mg of magnesium stearate, and an immediate release coating layer consisting essentially of about 7.5 mg phenylephrine hydrochloride and about 36 mg polyvinylalcohol-based polymer, wherein t is a value of hours up to 24 hours.

9. The composition according to claim 8, wherein the phenylephrine dissolution profile of the composition comprises a zero-order release rate.

\* \* \* \* \*